US011384376B2

(12) United States Patent
Nierth

(10) Patent No.: US 11,384,376 B2
(45) Date of Patent: Jul. 12, 2022

(54) REAGENTS AND METHODS FOR POST-SYNTHETIC MODIFICATION OF NUCLEIC ACIDS

(71) Applicant: Roche Molecular Systems, Inc., Pleasanton, CA (US)

(72) Inventor: Alexander Nierth, Dublin, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 358 days.

(21) Appl. No.: 16/423,657

(22) Filed: May 28, 2019

(65) Prior Publication Data

US 2020/0017895 A1 Jan. 16, 2020

Related U.S. Application Data

(60) Provisional application No. 62/678,927, filed on May 31, 2018.

(51) Int. Cl.
C12Q 1/68 (2018.01)
C07H 21/02 (2006.01)
C12P 19/34 (2006.01)
C12Q 1/6806 (2018.01)

(52) U.S. Cl.
CPC ............ *C12P 19/34* (2013.01); *C12Q 1/6806* (2013.01)

(58) Field of Classification Search
None
See application file for complete search history.

(56) References Cited

U.S. PATENT DOCUMENTS

| | | |
|---|---|---|
| 6,316,610 B2 | 11/2001 | Lee et al. |
| 6,875,850 B2 | 4/2005 | Heindl et al. |
| 7,166,478 B2 | 1/2007 | Stavrianopoulos et al. |
| 7,501,504 B2 | 3/2009 | Bodepudi et al. |
| 7,759,469 B2 | 7/2010 | Heindl et al. |
| 7,795,423 B2 | 9/2010 | Heindl |
| 9,140,706 B2 | 9/2015 | Antoulinakis, et al. |
| 9,169,283 B2 | 10/2015 | Wiessler et al. |
| 9,315,537 B2 | 4/2016 | Becker et al. |
| 2002/0147331 A1* | 10/2002 | Guzaev et al. ......... C07H 19/10 536/25.3 |
| 2003/0198980 A1 | 10/2003 | Greenfield et al. |
| 2010/0003189 A1* | 1/2010 | Tlsty et al. ...... G01N 33/57415 424/1.49 |
| 2012/0164643 A1* | 6/2012 | Bergmann et al. .. C12Q 1/6841 435/6.11 |
| 2013/0158243 A1 | 6/2013 | Ball |
| 2014/0058073 A1* | 2/2014 | Hoshino et al. ........ C09K 11/06 534/16 |
| 2017/0362640 A1* | 12/2017 | Pagani et al. .......... C12Q 1/689 |

FOREIGN PATENT DOCUMENTS

WO 2004074429 A2 9/2004

OTHER PUBLICATIONS

International Search Report and Written Opinion dated Jul. 15, 2019 in Application No. PCT/EP2019/063974, 17 pages.
Shoji et al., "Chemico-enzymatic synthesis of a new fluorescent-labeled DNA by PCR with a thymidine nucleotide analogue bearing an acridone derivative", Bioorganic & Medicinal Chemistry Letters, vol. 17 No. 3, 2007, p. 776-779.
Ferraboli S. et al., "One-lane chemical sequencing of 3'-fluorescent-labeled DNA", Analytical Biochemistry, 214 No. 2, 1993, p. 566-570.
Tous G. et al., "Preparation and chromatographic use of 5'-fluorescent-labelled DNA probes", Journal of Chromatography, vol. 444, 1988, p. 67-77.
Fink SR et al., "Fluorescent-labeled DNA probes applied to novel biological aspects of B-cell chronic lymphocytic leukemia", Leukemia Research, vol. 29 No. 3, 2005, p. 253-262.
Carter, J.D. et al., "Coupling Strategies for the Synthesis of Peptide-Oligonucleotide Conjugates for Patterned Synthetic Biomineralization", Journal of Nucleic Acids vol. 2011, Article ID 926595, 1-8.
D'Este, M. et al., "A systematic analysis of DMTMM vs EDC/NHS for ligation of amines to Hyaluronan in water", Carbohydrate Polymers, 2014, 108, 239-246.
El-Faham, A. et al., "Peptide Coupling Reagents, More than a Letter Soup", Chemical Reviews, 2011, 111, 6557-6602.
Falchi, A. et al., "4-(4,6-Dimethoxy[1,3,5]triazin-2-yl)-4-methyl-morpholinium Chloride (DMTMM): A Valuable Alternative to PyBOP for Solid Phase Peptide Synthesis", Synlett, 2000, No. 2, 275-277.
Jastrzabek, K. et al., "Benzyloxy Derivatives of Triazine-based Coupling Reagents Designed for an Efficient Solid Phase Peptide Synthesis on Polystyrene Resin", International Journal of Peptide Research and Therapeutics, 2007, vol. 13, Nos. 1-2, 229-236.
Kaminski, Z.J., et al., "N-Triazinylammonium Tetrafluoroborates. A New Generation of Efficient Coupling Reagents Useful for Peptide Synthesis", J. Am. Chem. Soc. 2005, 127, 16912-16920.
Kolesinska, B. et al., "The Effect of Counterion and Tertiary Amine on the Efficiency of NTriazinylammonium Sulfonates in Solution and Solid-Phase Peptide Synthesis", Eur. J. Org. Chem. 2015, 401-408.
Kunishima, M. et al., "Potent triazine-based dehydrocondensing reagents substituted by an amido group", Beilstein J. Org. Chem. 2016, 12, 1897-1903.
Kunishima, M. et al., "4-(4,6-Dimethoxy-1,3,5-triazin-2-yl)-4-methylmorpholinium Chloride: An Efficient Condensing Agent Leading to the Formation of Amides and Esters", Tetrahedron, 1999, 55, 13159-13170.

(Continued)

*Primary Examiner* — Bradley L. Sisson
(74) *Attorney, Agent, or Firm* — David J. Chang

(57) ABSTRACT

The present invention relates to compositions and methods (reagents and protocols) for the post-synthetic modification of nucleic acids obtained from solid-phase oligonucleotide synthesis with a label (such as fluorescent dyes). The coupling reagent is the triazine-based salt 4-(4,6-dimethoxy-1,3,5-triazin-2-yl)-4-methylmorpholinium (DMT-MM) in the presence of a counteranion.

17 Claims, 18 Drawing Sheets

(56) References Cited

OTHER PUBLICATIONS

Kunishima, M. et al., "Formation of carboxamides by direct condensation of carboxylic acids and amines in alcohols using a new alcohol- and water-soluble condensing agent: DMT-MM." Tetrahedron, 2001, 57, 1551-1558.
Raw, S.A., "An improved process for the synthesis of DMTMM-based coupling reagents", Tetrahedron Letters, 2009, 50, 946-948.
Zivanovic, A., "4-(4,6-Dimethoxy-1,3,5-triazin-2-yl)-4-methylmorpholinium Chloride", SYNLETT, 2012, 23, 2426-2427.

* cited by examiner

Atto490LS

| Source | N | Ct | | | Amplitude | | | Baseline | | | $K_{exp}$ | | |
|---|---|---|---|---|---|---|---|---|---|---|---|---|---|
| | | Average | SD | CV | Average | SD | CV | Average | SD | CV | Average | Std. Dev. | CV |
| DMT-MM labeled | 5 | 30.5 | 0.2 | 0.8% | 2.00 | 0.10 | 5% | 122 | 29 | 24% | 0.25 | 0.02 | 7% |
| NHS labeling | 5 | 30.9 | 0.2 | 0.7% | 1.28 | 0.05 | 4% | 68 | 21 | 31% | 0.17 | 0.01 | 4% |

Chromeo 494

| Source | N | Ct | | | Amplitude | | | Baseline | | | $K_{exp}$ | | |
|---|---|---|---|---|---|---|---|---|---|---|---|---|---|
| | | Average | SD | CV | Average | SD | CV | Average | SD | CV | Average | Std. Dev. | CV |
| DMT-MM labeled | 5 | 30.4 | 0.2 | 0.7% | 2.38 | 0.14 | 6% | 36 | 11 | 30% | 0.27 | 0.01 | 5% |
| NHS labeling | 5 | 30.4 | 0.2 | 0.8% | 1.91 | 0.11 | 6% | 30 | 8 | 28% | 0.23 | 0.01 | 5% |

Dy380XL

| Source | N | Ct | | | Amplitude | | | Baseline | | | $K_{exp}$ | | |
|---|---|---|---|---|---|---|---|---|---|---|---|---|---|
| | | Average | SD | CV | Average | SD | CV | Average | SD | CV | Average | Std. Dev. | CV |
| DMT-MM labeled | 5 | 28.9 | 0.3 | 1.2% | 2.39 | 0.16 | 6.8% | 16 | 5 | 28% | 0.24 | 0.02 | 10% |
| NHS labeling | 5 | 29.8 | 0.5 | 1.6% | 1.56 | 0.14 | 8.7% | 10 | 2 | 25% | 0.18 | 0.02 | 9% |

Dy395XL

| Source | N | Ct | | | Amplitude | | | Baseline | | | $K_{exp}$ | | |
|---|---|---|---|---|---|---|---|---|---|---|---|---|---|
| | | Average | SD | CV | Average | SD | CV | Average | SD | CV | Average | Std. Dev. | CV |
| DMT-MM labeled | 5 | 28.7 | 0.3 | 0.9% | 2.89 | 0.20 | 7% | 27 | 6 | 21% | 0.28 | 0.02 | 7% |
| NHS labeling | 5 | 30.2 | 0.4 | 1.4% | 1.25 | 0.27 | 22% | 14 | 3 | 25% | 0.15 | 0.03 | 21% |

FIG. 8

| Oligo # | Dye | Dye Lot # | Calculated MW [g/mol] | Measured MW [g/mol] |
|---|---|---|---|---|
| 171742 | Dy396XL | E19-07100 | 9628.76 | 9627.7 |
| 171743 | Dy396XL | E19-08139 | 9628.76 | 9627.4 |
| 171744 | Dy396XL | E19-07100/E19-08139 | 9628.76 | 9627.5 |
| 171745 | Dy396XL | E19-07100 | 10645.38 | 10646.4 |
| 171746 | Dy396XL | E19-08139 | 10645.38 | 10646.0 |
| 171747 | Dy396XL | E19-07100/E19-08139 | 10645.38 | 10646.1 |

| Probes | N | Ct | | | Amplitude | | | Baseline | | | $K_{exp}$ | | |
|---|---|---|---|---|---|---|---|---|---|---|---|---|---|
| | | Average | SD | CV | Average | SD | CV | Average | SD | CV | Average | Std. Dev. | CV |
| 171742 + 171745 | 5 | 28.2 | 0.4 | 1.6% | 2.52 | 0.19 | 7.5% | 72 | 14 | 18.7% | 0.26 | 0.02 | 9.6% |
| 171743 + 171746 | 5 | 28.2 | 0.4 | 1.5% | 2.61 | 0.25 | 9.6% | 64 | 8 | 12.5% | 0.26 | 0.04 | 14.3% |

FIG. 11

REAGENTS AND METHODS FOR POST-SYNTHETIC MODIFICATION OF NUCLEIC ACIDS

CROSS REFERENCE TO RELATED APPLICATIONS

This application claims the benefit of priority to U.S. Provisional Application No. 62/678,927 filed on May 31, 2018, which is hereby incorporated in its entirety by reference.

FIELD OF THE INVENTION

The present invention relates generally to the field of nucleic acid chemistry, and particularly to methods and compositions for the post-synthetic modification of nucleic acids with a label using a coupling reagent.

BACKGROUND OF THE INVENTION

Many procedures employed in biomedical research and recombinant DNA technology rely on the use of labeled nucleotide or polynucleotide derivatives. In order for a modified nucleotide to be suitable as a labeled form of a naturally occurring nucleotide, several criteria must typically be satisfied. First, the modified compound must contain a substituent or probe that is unique (i.e., not normally found associated with nucleotides or polynucleotides). Second, the probe must react specifically with chemical or biological reagents to provide a sensitive detection system. Third, the analog must be an efficient substrate for commonly studied nucleic acid enzymes, since numerous practical applications require that the analog be enzymatically metabolized (e.g., the analog must function as a substrate for nucleic acid polymerases). For this purpose, probe moieties should not be placed on ring positions that sterically or otherwise interfere with the normal Watson-Crick hydrogen bonding potential of the bases. In such cases, the substituents can yield compounds that are inactive as polymerase substrates. Fourth, the detection system should be capable of interacting with probe substituents incorporated into both single stranded and double stranded polynucleotides in order to be compatible with nucleic acid hybridization methodologies. Fifth, the physical and biochemical properties of polynucleotides containing small numbers of probe substituents should not be significantly altered so that current procedures using hybridization probes need not be extensively modified. This criterion must be satisfied whether the probe is introduced by enzymatic or direct chemical means. Finally, the linkage that attaches the probe moiety should withstand all experimental conditions to which normal nucleotides and polynucleotides are routinely subjected (e.g., extended hybridization times at elevated temperatures, phenol and organic solvent extraction, or electrophoresis).

Methods for labeling biomolecules with fluorescent, luminescent, quenching or phosphorescent dyes, or with affinity tags have become indispensable in the modern life sciences, and for those conjugation strategies, it is important that they allow the site-specific post-synthetic coupling of complex molecules under mild conditions. While N-hydroxysuccinimide (NETS) ester chemistry has dominated the labeling of both protein and nucleic acid molecules, ease and cost considerations have prompted the need for new labeling methods that should be suitable for small chemically synthesized oligonucleotides as well as for longer enzymatically amplified DNA strands.

In recent years, triazine-based compounds initially developed for natural product and peptide synthesis (Kunishima et al., Tetrahedron 55, 13159-13170, 1999) have come to prominence as effective coupling agents, finding applications in amidation, esterification, glycosidation and phosphonylation reactions. Despite the high reactivity of 4-(4,6-dimethoxy-1,3,5-triazin-2-yl)-4-methylmorpholinium (DMT-MM) for the condensation of carboxy- and amino-groups to amides, it is remarkably stable in water and alcohols. As such, DMT-MM is an attractive alternative for other water-compatible reagents such as the carbodiimide EDC [N-(3-dimethyl-aminopropyl)-N'-ethylcarbodiimide], which can react with phosphates and is prone to decomposition at low pH, or the peptide coupling reagent TBTU (2-(1H-benzotriazole-1-yl)-1,1,3,3-tetramethylaminium tetrafluoroborate).

SUMMARY OF THE INVENTION

The present invention provides for methods for the post-synthetic modification of nucleic acids obtained from solid-phase oligonucleotide synthesis with a label (such as fluorescent dyes) using 4-(4,6-dimethoxy-1,3,5-triazin-2-yl)-4-methylmorpholinium (DMT-MM) salts as coupling reagents. The chemical structure of DMT-MM is shown on FIG. 1. Therefere in one aspect, the present invention relates to a method for post-synthetic modification of a nucleic acid with a label comprising the steps of: (a) preparing an amino-modified nucleic acid molecule comprising one or more amino-modifications (b) activating a carboxy-modified label with DMT-MM; and (c) reacting the amino-modified nucleic acid molecule with the activated carboxy-modified label to generate a labeled nucleic acid molecule. In one embodiment, the activating step involves DMT-MM in the presence of a counter anion. In one embodiment, the counter anion is selected from the group consisting of tetrafluoroborate ($BF_4^-$), hexafluorophosphate ($PF_6^-$), benzenesulfonate ($CH_5SO_3^-$), bis(trifluoromethanesulfonyl)imide (($N[SO_2(CF_3)]_2$)), bromide ($Br^-$), 10-camphorosulfonate, chloride ($Cl^-$), iodide ($I^-$), methanesulfonate (mesylate, $CH_3SO_3^-$), perchlorate ($ClO_4^-$), phosphate ($PO_4^{3-}$), sulfate ($SO_4^{2-}$), tetrachloroaluminate ($AlCl_4^-$), tetrakis[3,5-bis(trifluoromethyl)phenyl]borate ($B[3,5-(CF_3)_2C_6H_3]_4^-$), tetrakis (hexafluoroisopropyl)aluminate $Al[OC(CF_3)_3]_4^-$), tetrakis (pentafluorophenyl)borate [$B(C_6F_5)_4^-$], p-toluenesulfonate (tosylate, $CH_3C_6H_4SO_3^-$), trifluoromethanesulfonate (triflate, $CF_3SO_3^-$). In one embodiment, the counter anion is tetrafluoroborate ($BF_4^-$) or hexafluorophosphate ($PF_6^-$). In one embodiment, the nucleic acid molecule is an oligonucleotide. In another embodiment, the oligonucleotide has a length of between 3 and 500 nucleotides. In another embodiment, the oligonucleotide is amino-modified at the 5' or at the 3' terminus. In another embodiment, the oligonucleotide is amino-modified internally. In yet another embodiment, the label is selected from the group consisting of a fluorescent dye, a luminescent dye, a quenching dye, a phosphorescent dye and an affinity tag. In one embodiment, the label is a fluorescent dye. In another embodiment, the fluorescent dye is inherently incompatible with phosphoramidite-based DNA synthesis. In yet another embodiment, the fluorescent dye contains a sulfonate moiety. In one embodiment, the stoichiometry of the amino-modified oligonucleotide and the activated carboxy-modified label is 1:3 or between 1:3 and 1:1.5 if the oligonucleotide is less than 100 nucleotides in length. In another embodiment, the activated carboxy-modified label is used in 2-20-fold molar excess of the amino-modified oligonucleotide if the oligonucleotide is more than 100 nucleotides in length. In one embodiment, the oligonucleotide is synthesized using phosphoramidite-based DNA synthesis. In one embodiment, the oligonucleotide is purified after synthesis. In another embodiment, the oligonucleotide is not purified after synthesis. In one embodiment, the methods of the steps are practiced during synthesis of the oligonucleotide wherein the oligonucleotide is bound on a solid support. In one embodiment, the nucleic acid molecule is single-stranded. In another embodiment, the nucleic acid molecule is double-stranded. In another embodiment, the nucleic acid molecule is an enzymatically amplified product. In another embodiment, the nucleic acid molecule is selected from the group consisting of DNA, RNA, LNA, PNA, a nucleic acid analog, and mixtures of DNA, RNA, LNA, PNA and a nucleic acid analog.

The present invention also provides for a kit comprising a labeled nucleic acid that is labeled by a method comprising the steps of (a) preparing an amino-modified nucleic acid molecule comprising one or more amino-modifications (b) activating a carboxy-modified label with DMT-MM; and (c) reacting the amino-modified nucleic acid molecule with the activated carboxy-modified label to generate a labeled nucleic acid molecule.

BRIEF DESCRIPTION OF THE DRAWINGS

FIG. 8 is a table that shows the derived threshold cycle ($C_t$) values, fluorescence baselines, signal amplitudes, and experimental rate constant values ($K_{exp}$) from the qPCR experiments described in Example 2.

FIG. 10B shows the mass spectrometry analyses of purified DNA oligonucleotide probes that were obtained by large-scale labeling reactions using DMT-MM described in Example 3.

FIG. 11 is a table that shows the derived threshold cycle ($C_t$) values, fluorescence baselines, signal amplitudes, and experimental rate constant values ($K_{exp}$) from the qPCR experiments described in Example 3. For each qPCR two probe sequences labeled with Dy396XL were combined and hybridize to two different regions of the target DNA sequence.

DETAILED DESCRIPTION OF THE INVENTION

Definitions

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

As used herein and unless otherwise indicated, the term "alkyl group" means a saturated, monovalent, unbranched or branched hydrocarbon chain. Examples of alkyl groups include, but are not limited to, $C_1$-$C_6$ alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2 pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

As used herein and unless otherwise indicated, the term —O-alkyl (or alkyl-O—) means an "alkoxy group", wherein alkyl is as defined above. An alkoxy group can be unsubstituted or substituted with one or more suitable substituents. The alkyl chain of an alkyloxy group can be, for example, from 1 to 6 carbon atoms in length.

As used herein and unless otherwise indicated, the term "metal" refers to a group I or group II metal, including but not limited to $Li^+$, $Na^+$, $Mg^{2+}$, or $Mn^{2+}$.

As used herein and unless otherwise indicated, the term "linking group" and "linker" are used interchangeably and refer to a moiety of a detectable label capable of covalently bonding a base with a label, e.g., forming a "linkage" that connects the nucleoside, nucleotide or nucleic acid to the label. Examples of linkers include, but are not limited to, O, S, or NH. Optionally, the linking group or linker is a covalent bond (i.e., the label is covalently bonded to the base).

Figure 1:
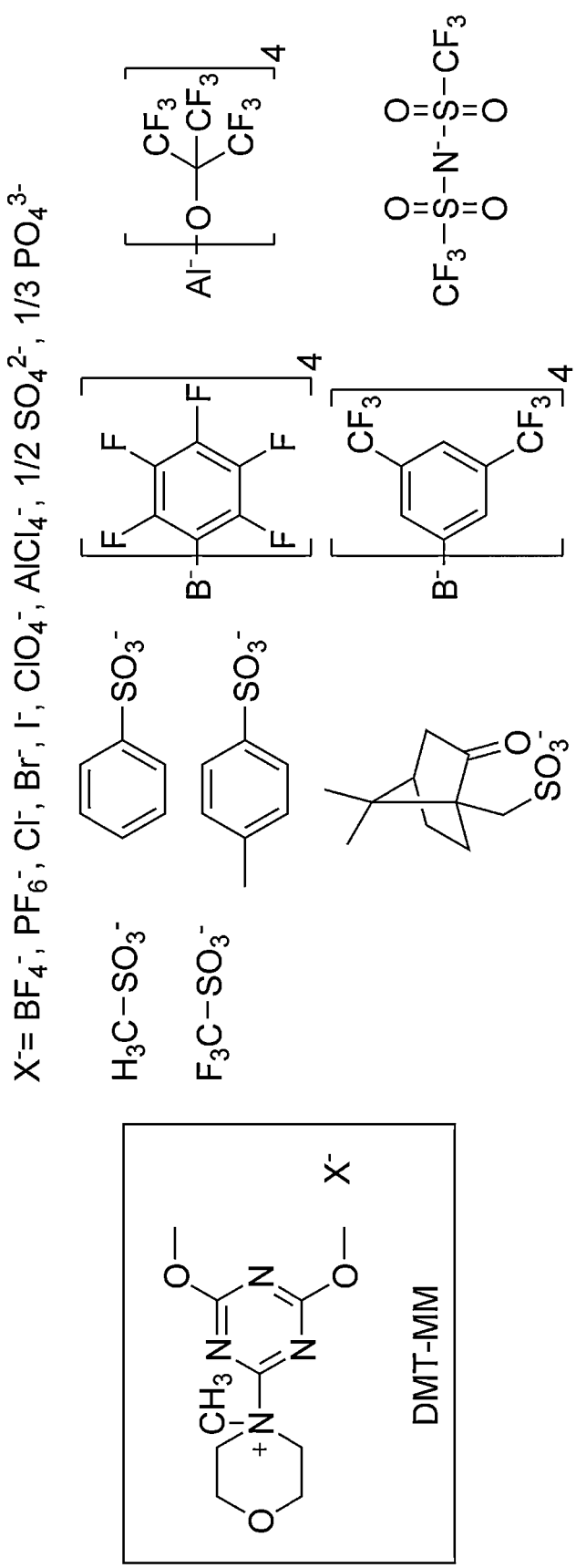
FIG. 1 shows the structure of 4-(4,6-dimethoxy-1,3,5-triazin-2-yl)-4-methylmorpholinium (DMT-MM) and selected examples of its counter anions.
Figure 2A:
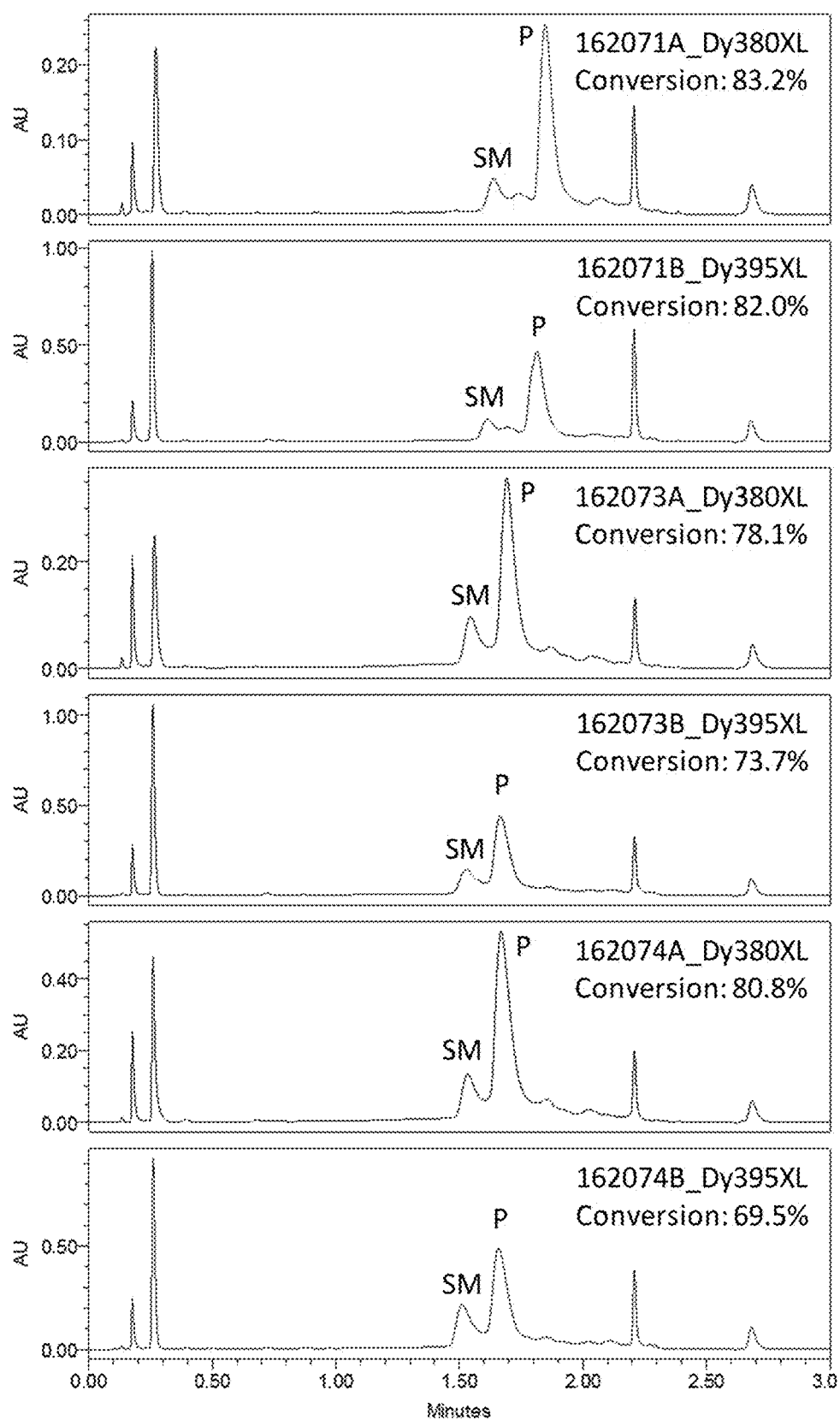
FIG. 2A shows the UPLC analysis of 5'-labeling reactions. Unpurified oligonucleotides from solid-phase DNA synthesis were labeled with Dy380XL or Dy395XL carboxylic acids at the 5'-end. Each of the 30mer (162071) and 33mer (162073, 162074) oligonucleotides contained a 3'-BHQ-2 quencher. Reaction conversions (%) were determined by comparing the peak areas of starting material (SM) and product (P).
Figure 2B:
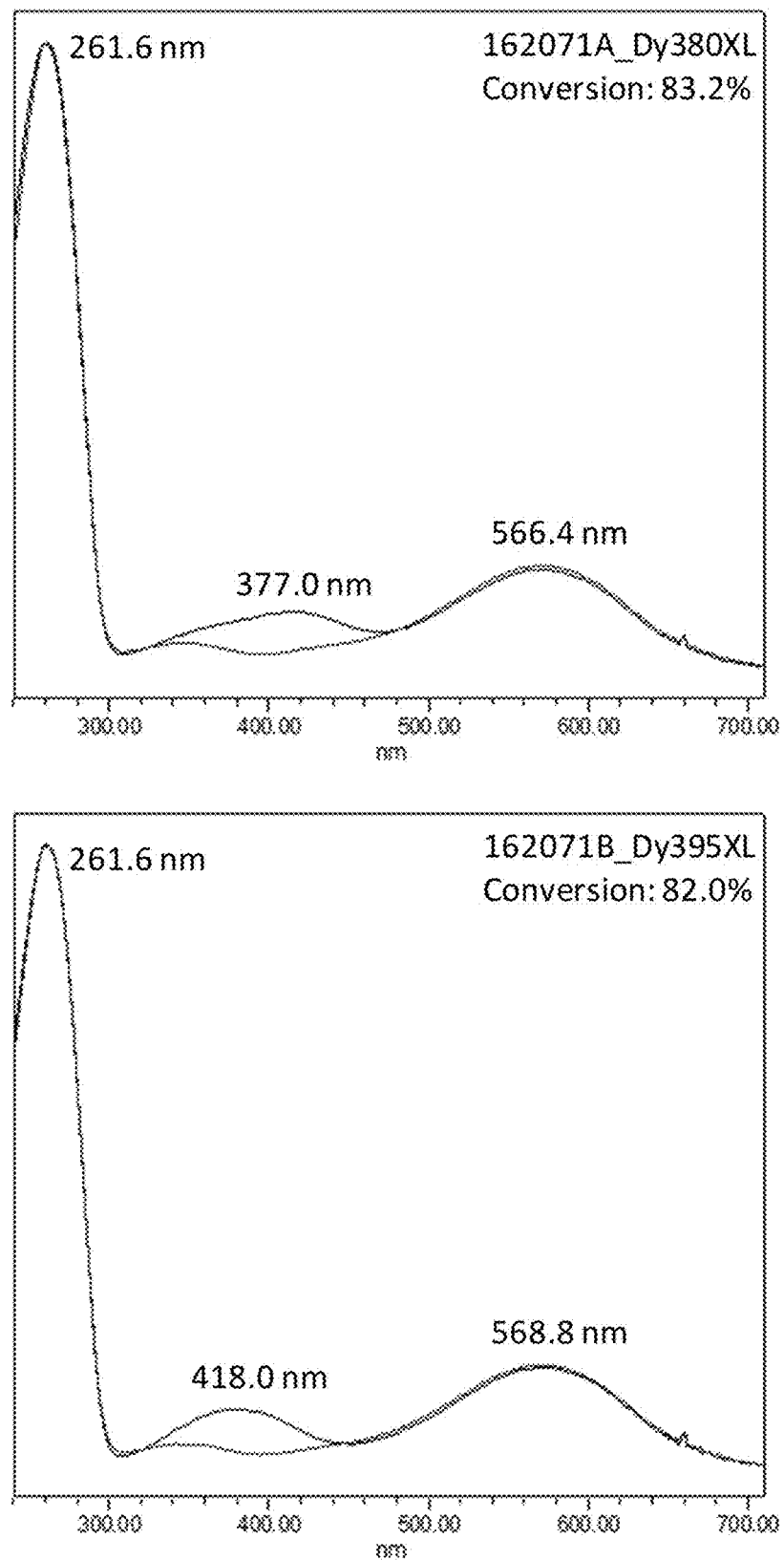
FIG. 2B shows overlayed absorption spectra of oligonucleotides before and after labeling with Dy380XL (top) and Dy395XL (bottom). The spectra were extracted from the top two chromatograms in FIG. 2A (162071A and B).
Figure 3:
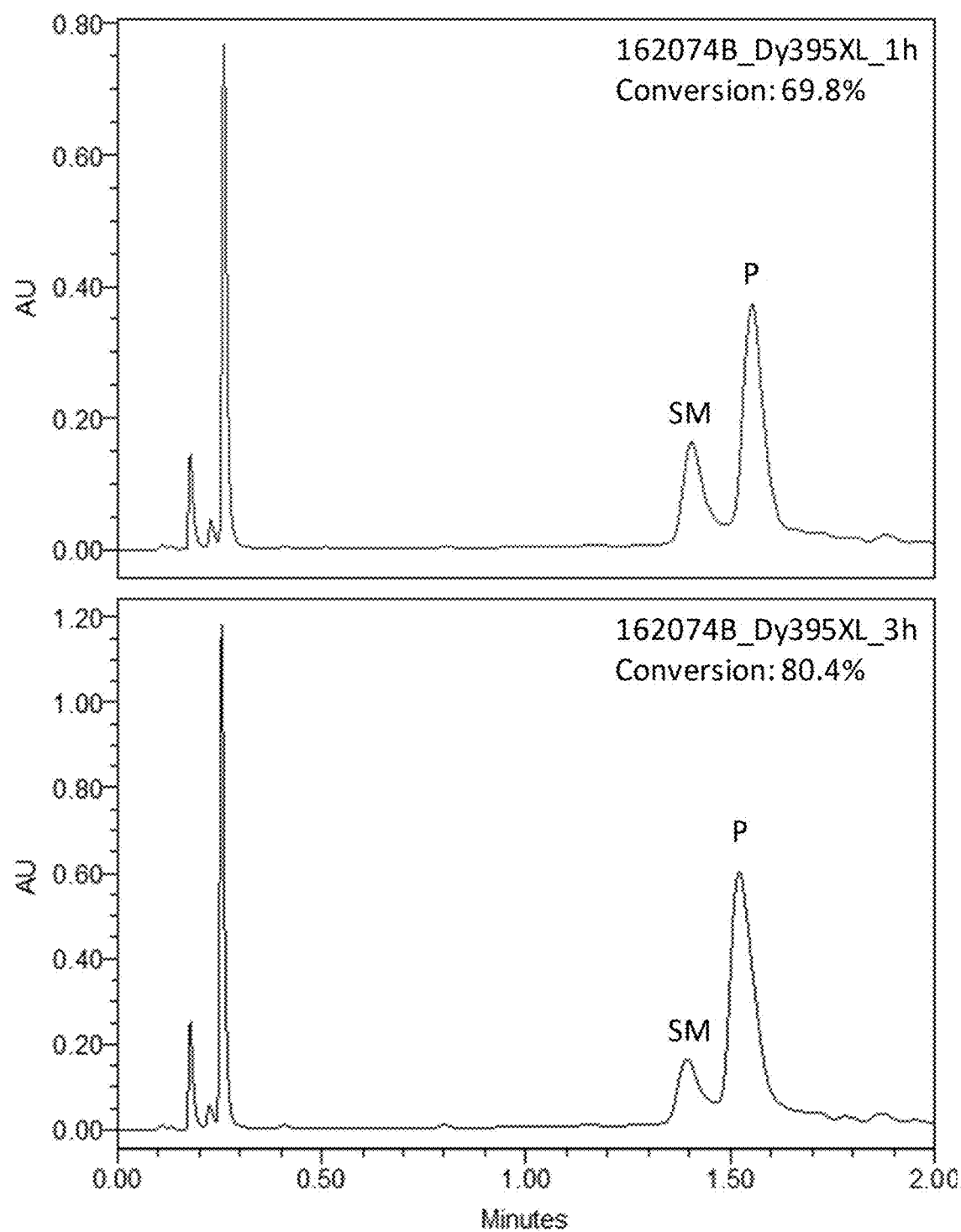
FIG. 3 shows the UPLC analysis of a 5'-labeling reaction with Dy395XL, a fluorescent dye with very low solubility in organic solvents. Reaction conditions were the same as for sample No. 162074B in FIG. 2A, however with 50% water during the preactivation step. The reaction conversion increased from 69.8% to 80.4%, which was determined by comparing the peak areas of starting material (SM) and product (P).
Figure 4A:
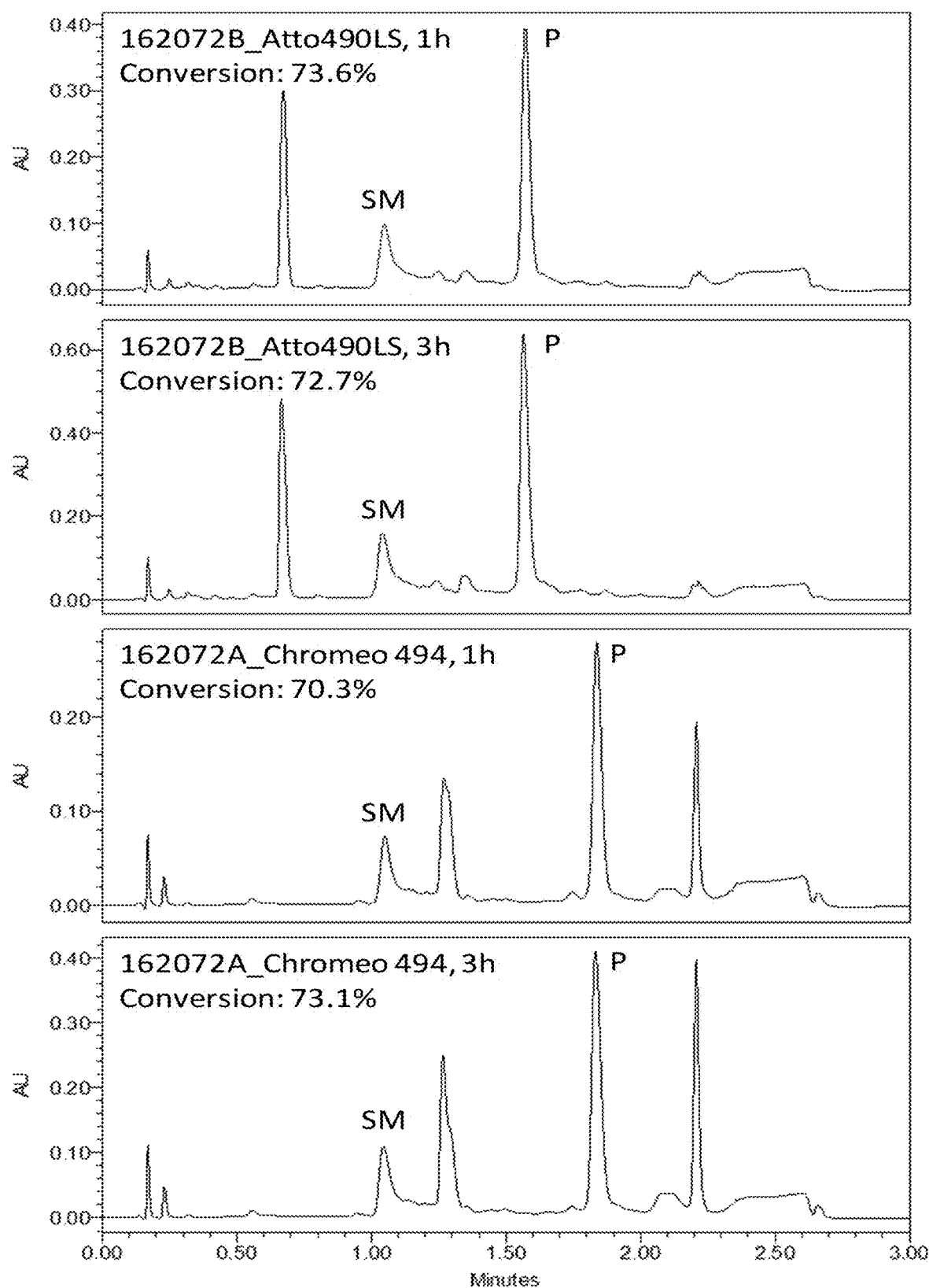
FIG. 4A shows the UPLC chromatograms of 5'-labeling reactions at two time points (1.0 h, 3.0 h). Unpurified 29mer oligonucleotide was labeled with Atto490LS and Chromeo™ 494 carboxylic acids at the 5'-end. Both oligonucleotides contained a 3'-BHQ-2 quencher. Reaction conversions (%) were determined by comparing the peak areas of starting material (SM) and product (P).
Figure 4B:
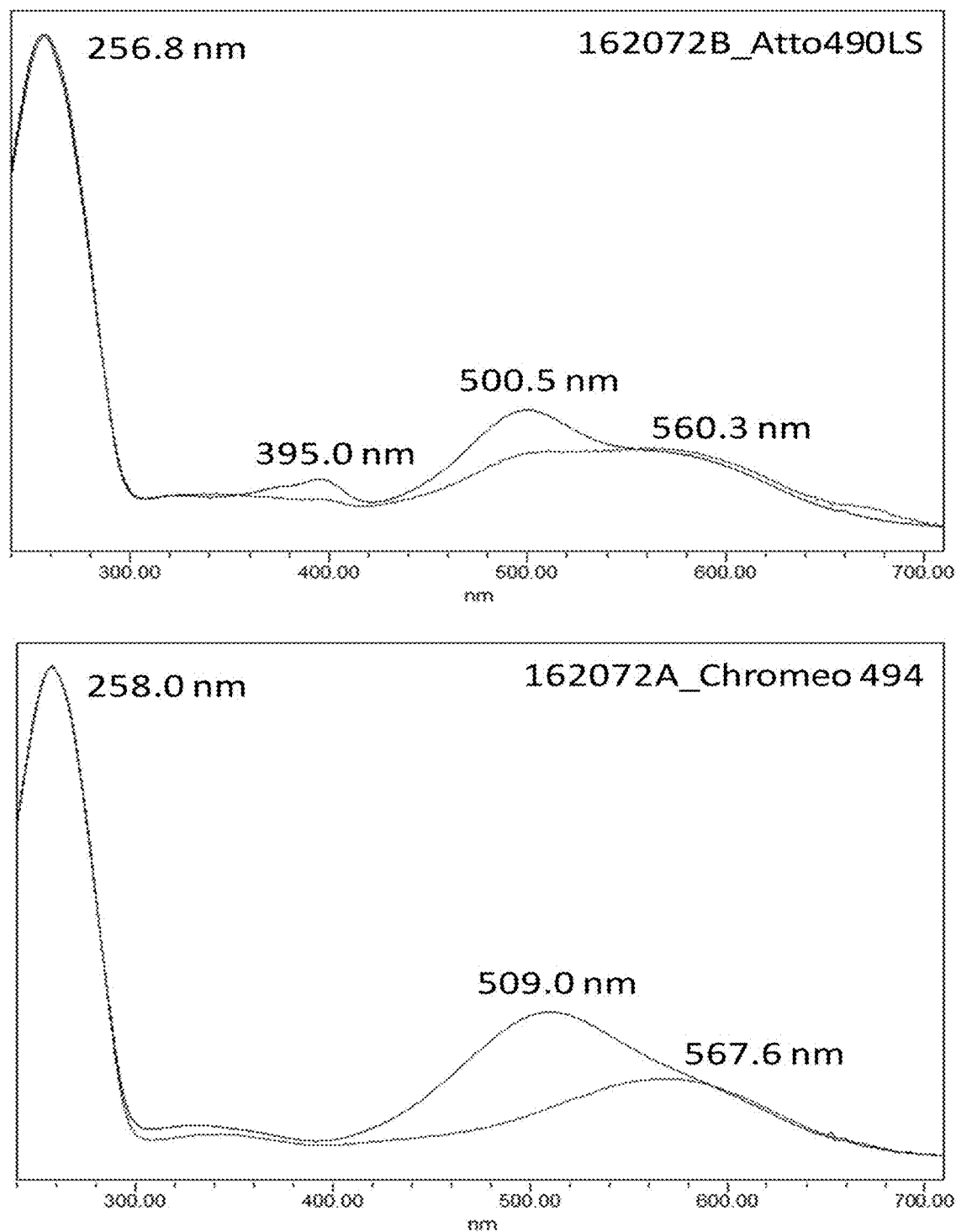
FIG. 4B shows overlayed absorption spectra of oligonucleotides before and after labeling with Atto490LS (top) and Chromeo™ 494 (bottom). The spectra were extracted from the top two chromatograms in FIG. 4A (162072B and A).
Figure 5:
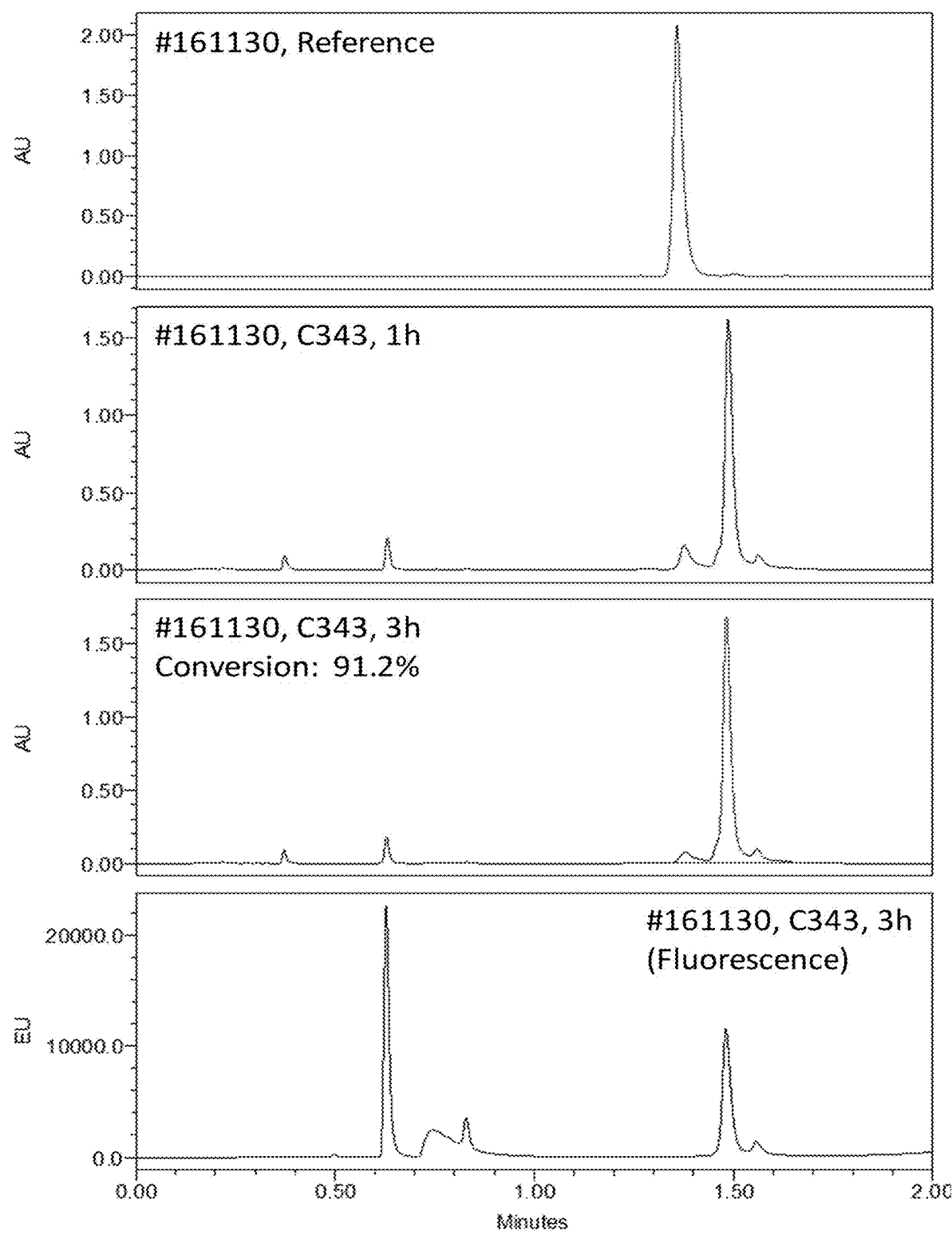
FIG. 5 shows a representative example for labeling a DNA oligonucleotide sequence at an internal position. Shown are UPLC chromatograms of a pre-purified 55mer DNA-LNA hybrid oligonucleotide (161130) with 5'-BHQ-2 quencher that was labeled with C343 carboxylic acid. Samples were taken before reaction (Reference), and after 1.0 h, and 3.0 h. Reaction conversions (%) were determined by comparing the peak areas of starting material (SM) and product (P).

As used herein and unless otherwise indicated, the term "counterion" or "counter anion" refers to an ion that is stable and synthetically accessible. Examples of counter anions are shown on FIG. 1 and include, but are not limited to tetrafluoroborate ($BF_4^-$), hexafluorophosphate ($PF_6^-$), benzenesulfonate ($CH_5SO_3^-$), bis(trifluoromethanesulfonyl)imide (($N[SO_2(CF_3)]_2)^-$), bromide ($Br^-$), 10-camphorosulfonate, chloride ($Cl^-$), iodide ($I^-$), methanesulfonate (mesylate, $CH_3SO_3^-$), perchlorate ($ClO_4^-$), phosphate ($PO_4^{3-}$), sulfate ($SO_4^{2-}$), tetrachloroaluminate ($AlCl_4^-$), tetrakis[3,5-bis(trifluoromethyl)phenyl]borate ($B[3,5-(CF_3)_2C_6H_3]_4^-$), tetrakis (hexafluoroisopropyl)aluminate $Al[OC(CF_3)_3]_4^-$), tetrakis (pentafluorophenyl)borate [$B(C_6F_5)_4^-$], p-toluenesulfonate (tosylate, $CH_3C_6H_4SO_3^-$), trifluoromethanesulfonate (triflate, $CF_3SO_3^-$). The counteranion can be any weakly-coordinating or non-coordinating anion.

As used herein, the term "non-coordinating anion" is used interchangeably with the term "weakly-coordinating anion" and means an anion which either does not coordinate to a cation or which is only weakly coordinated to a cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the DMT-MM cation in the sense of balancing its ionic charge at +1, and yet retain sufficient lability to permit displacement during reaction.

As used herein, a substance that is "biologically compatible" is not toxic as used, and does not have a substantially deleterious effect on biomolecules.

As used herein and unless otherwise indicated, the term "nucleobase" refers to adenine, cytidine, guanine, thymine, or uracil.

As used herein and unless otherwise indicated, the term "nucleobase analog" refers to a substituted or unsubstituted nitrogen-containing parent heteroaromatic ring that is capable of forming Watson-Crick hydrogen bonds with a complementary nucleobase or nucleobase analog. Preferably, the nucleobase analog is a purine, deazapurine or pyrimidine. Exemplary nucleobase analogs include, but are not limited to, 7-deazaadenine, inosine, nebularine, nitropyrrole, nitroindole, 2-aminopurine, 2,6-diaminopurine, hypoxanthine, pseudouridine, 5-propynylcytidine, isocytidine, isoguanine, 7-deazaguanine, 2-thiopyrimidine, 6-thioguanine, 4-thiothymine, 4-thiouracil, $O^6$-methyl guanine, $N^6$-methyl adenine, $O^4$-methyl thymine, 5,6-dihydrothymine, 5,6-dihydrouracil, 4-methylindole, ethenoadenine, etc. Additional exemplary nucleobase analogs can be found in Fasman, 1989, Practical Handbook of Biochemistry and Molecular Biology, pp. 385-394, CRC Press, Boca Raton, Fla., and the references cited therein, incorporated herein by reference.

As used herein and unless otherwise indicated, the term "nucleoside" refers to a compound consisting of a nucleobase covalently linked to the Cr carbon of a substituted or unsubstituted ribose sugar. Typical substituted ribose sugars include, but are not limited to, those in which one or more of its carbon atoms, preferably one and most preferably the 3' carbon atom, is substituted with one or more of the same or different —R, —OR, —NRR or halogen groups, where each R is independently —H, ($C_1$-$C_6$) alkyl or ($C_5$-$C_{14}$) aryl. Particularly preferred ribose sugars are ribose, 2'-deoxyribose, 2',3'-dideoxyribose, 3'-haloribose, 3'-fluororibose, 3'-chlororibose, 3'-alkylribose, etc. When the nucleobase is A or G, the ribose sugar is attached to the $N^9$ position of the nucleobase. Where the nucleobase is C, T or U, the pentose sugar is attached to the $N^1$ position of the nucleobase (see, e.g., Kornberg and Baker, 1992, DNA Replication, 2nd Ed., Freeman and Company, San Francisco).

As used herein and unless otherwise indicated, the term "nucleoside analog" refers to a nucleoside in which the nucleobase, the ribose sugar, or both, are replaced with their respective analogs. Exemplary nucleobase analogs are those previously defined. Exemplary ribose sugar analogs include, but are not limited to, substituted or unsubstituted furanoses with more or fewer than five members per ring, e.g., erythroses and hexoses and substituted or unsubstituted 3-6 carbon acyclic sugars. Typical substituted furanoses and acyclic sugars are those in which one or more of the carbon atoms are substituted with one or more of the same or different —R, —OR, NRR or halogen groups, where each R is independently H, ($C_1$-$C_6$) alkyl or ($C_5$-$C_{14}$) aryl.

As used herein and unless otherwise indicated, the term "nucleotide" refers to a nucleoside in which one or more, typically one, of the ribose carbons is substituted with a phosphate ester having the formula:

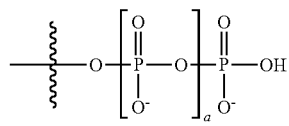

where a is an integer from 0 to 4. Preferably, a is 2 and the phosphate ester is attached to the 3' or 5'-carbon of the ribose, e.g., ribose 3'-triphosphate, 2'-deoxyribose 3'-triphosphate, ribose 5'-triphosphate, 2'-deoxyribose 5'-triphosphate, 3'-haloribose 5'-triphosphate, 3'-alkylribose 5'-triphosphate, 2',3'-dideoxyribose 5'-triphosphate, etc.

As used herein and unless otherwise indicated, the terms "nucleotide derivative" and "nucleotide analog" can be used interchangeably and refer to a nucleotide in which the nucleobase, the ribose sugar and/or one or more of the phosphate esters is replaced with its respective analog. Exemplary nucleobase and ribose sugar analogs are those previously described in conjunction with nucleoside analogs. Exemplary phosphate ester analogs include, but are not limited to alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, peptide nucleic acid (PNA) monomers, etc., including any associated counterions, if present.

As used herein and unless otherwise indicated, the term "nucleoside or nucleotide" refers to nucleosides and/or nucleotides and/or mixtures thereof.

As used herein and unless otherwise indicated, the term "nucleic acid" refers to a linear polymeric chain of nucleoside monomer units that are covalently connected to one another by phosphate ester internucleotide linkages. Unless stated otherwise, "nucleic acid" as used herein includes polymers of any length, including oligonucleotides, nucleic acids and nucleic acids as those terms are commonly used in the art. Thus, nucleic acids according to the invention can range in size from a few monomer units (e.g., 4 to 40), to several hundreds of monomer units, to several thousands of monomer units, or even more monomer units. Such nucleic acids can also be described herein in terms of their functions, such as primer or probe. Whenever a nucleic acid is represented by a sequence of letters, e.g., "ATGCCTG", it will be understood that the sequence is presented in the 5'→3' direction. Unless otherwise indicated, nucleic acids whose sequences are described herein are 2'-deoxyribonucleic acids.

"Oligonucleotides" and "modified oligonucleotides" according to the invention may be synthesized as principally described in the art and known to the expert in the field. Methods for preparing oligomeric compounds of specific sequences are known in the art, and include, for example, cloning and restriction of appropriate sequences and direct chemical synthesis. Chemical synthesis methods may include, for example, the phosphotriester method described by Narang, S. A., et al., Methods in Enzymology 68 (1979) 90-98, the phosphodiester method disclosed by Brown, E. L., et al., Methods in Enzymology 68 (1979) 109-151, the phosphoramidite method disclosed in Beaucage et al., Tetrahedron Letters 22 (1981) 1859 and U.S. Pat. No. 4,415,732, the H-phosphonate method disclosed in Garegg, et al., Chem. Scr. 25 (1985) 280-282 and the solid support method disclosed in U.S. Pat. No. 4,458,066, all of which are incorporated by reference for all purposes as if fully set forth herein.

As used herein and unless otherwise indicated, the term "nucleic acid analog" refers to a nucleic acid in which at least one nucleoside monomer unit is a "nucleoside analog" and/or at least one phosphate ester internucleotide linkage is a phosphate ester analog, as defined above under "nucleotide analog." Preferred classes of nucleic acid analogs are those in which the sugar and internucleotide linkages are replaced with an uncharged, neutral amide group, such as a morpholino carbamate and peptide nucleic acids ("PNA"). Preferred PNAs are those having a N-(2-aminoethyl) glycine amide backbone (see, e.g., Nielsen et al., 1991, Science 254:1497-1500).

As used herein, the term "amino-modified oligonucleotide" refers to an oligonucleotide that is modified with an amino group, or multiple amino groups, capable of reacting with a carboxy moiety (for example, a carboxy moiety on a label). Conversely, the term "carboxy-modified oligonucleotide" refers to an oligonucleotide that is modified with a carboxy group, or multiple carboxy groups, capable of reacting with an amino moiety (for example, an amino moiety on a label). Therefore for the purposes of the present invention, the amino and carboxy functional groups may be reversed for labeling purposes.

The amino-modification may comprise the addition of a variety of moieties that comprise one or more primary or secondary amines, or the modification may comprise the addition of one or more primary or secondary amines. Thus, the amino-modification may comprise the general formula [O]—$Z_n$, where [O] is the oligonucleotide; Z, at each occurrence, is chosen from $NH_2$, NHR, $RNH_2$, or RNHR; n is a non-zero integer; and R is independently and at each occurrence chosen from hydrocarbyl or substituted hydrocarbyl groups. For clarity, it is understood that where R is a divalent group, such a divalent R group may be a hydrocarbylene or substituted hydrocarbylene group including but not limited to an alkylene or substituted alkylene group. Where R is a monovalent group, R may be any number of hydrocarbyl or substituted hydrocarbyl groups, including but not limited to alkyl and substituted alkyl groups. R, when a monovalent group, may also be any number of protecting groups commonly known in the art, such as those described in Protective Groups in Organic Synthesis (Green, Wuts; $3^{rd}$ ed., 1999, John Wiley & Sons, Inc.), which is incorporated by reference for all purposes as if fully set forth herein. The oligonucleotide may be amino-modified at any position within the oligonucleotide. In some embodiments, the amino-modification is at the 5' terminus or at the 3' terminus. In other embodiments, the amino-modification is at one or more internal positions within the oligonucleotide. Oligonucleotides including amino-modified termini may be prepared using methods and reagents commonly employed in the art. For example, an oligonucleotide with an amino-modification at the 5' terminus may be prepared using various linkers (also known in the art as modifiers) including but not limited to $C_2$-$C_{12}$ amino linkers or amino protected derivatives thereof. Examples of $C_2$-$C_{12}$ amino linkers or amino protected derivatives thereof include, but are not limited to, 2-[2-(4-monomethoxytrityl)aminoethoxy]ethyl (2-cyanoethyl)-N,N-diisopropyl-) phosphoramidite (a $C_5$ MMT amino linker), 6-(4-monomethoxytritylamino)hexyl [(2-cyanoethyl)-(N,N-diisopropyl)]phosphoramidite (a $C_6$ MMT amino linker), 6-(trifluoroacetylamino)hexyl[(2-cyanoethyl)-(N,N-diisopropyl)]phosphoramidite (a $C_6$ TFA amino linker), 7-(4-monomethoxytritylamino)heptyl[(2-cyanoethyl)-(N,N-diisopropyl)]phosphoramidite (a $C_7$ MMT amino linker), 12-(4-monomethoxytritylamino)dodecyl[(2-cyanoethyl)-(N,N-diisopropyl)]phosphoramidite (a $C_{12}$ MMT amino linker). In yet other embodiments, the oligonucleotide includes one or more amino-modifications at a position other than the 3' or the 5' termini. For example, the oligonucleotide may include amino modifying groups directly attached, or otherwise tethered to one or more bases of the oligonucleotide. Such amino-modified oligonucleotides may be prepared using any number of phosphoramidites commonly known in the art, including but not limited to: an amino $C_6$ dT (e.g., 5'-dimethoxytrityl-5-[N-

(trifluoroacetylaminohexyl)-3-acrylimido]-2'-deoxyuridine, 3'-[(2-cyanoethyl)-(N,N-diisopropyl)]phosphoramidite, 5'-dimethoxytrityl-5-[N-((9-fluorenylmethoxycarbonyl)-aminohexyl)-3-acryl-imido]-2'-deoxyuridine, 3'-[(2-cyanoethyl)-(N,N-diisopropyl)]phosphoramidite and the like); an amino $C_6$ dA (e.g., 5'-dimethoxytrityl-$N^6$-benzoyl-$N^8$-[6-(trifluoroacetylamino)-hex-1-yl]-8-amino-2'-deoxyadenosine-3'-[(2-cyanoethyl)-(N,N-diisopropyl)]phosphoramidite); an amino $C_6$ dG (e.g., 5'-dimethoxytrityl-N2-(N,N-dimethylaminomethylidene)-$N^8$-[6-(trifluoroacetylamino)-hex-1-yl]-8-amino-2'-deoxyguanosine-3'-[(2-cyanoethyl)-(N,N-diisopropyl)]phosphoramidite), an amino $C_6$ dC (e.g., 5'-dimethoxytrityl-N-dimethylformamidine-5-[N-(trifluoroacetylaminohexyl)-3-acrylimido]-2'-deoxycytidine, 3'-[(2-cyanoethyl)-(N,N-diisopropyl)]phosphoramidite), and/or an amino $C_2$ dT (e.g., 5'-dimethoxytrityl-5-[N-(trifluoroacetylaminoethyl)-3-acrylimido]-2'-deoxyuridine, 3'-[(2-cyanoethyl)-(N,N-diisopropyl)]phosphoramidite). For clarity, it is understood that any phosphoramidites which include protected amino groups, including but not limited to those indicated above, may be optionally deprotected after the synthesis of the amino-modified oligonucleotide, using deprotection methods known in the art.

As used herein and unless otherwise indicated, the term "protecting group" refers to a group that is reversibly attached to a hydroxyl or amine moiety that renders the hydroxyl or amine moiety unreactive during a subsequent reaction(s) and that can be selectively cleaved to regenerate the hydroxyl or amine moiety once its protecting purpose has been served. Examples of protecting groups are found in Greene, T. W., Protective Groups in Organic Synthesis, 3rd edition (1999), incorporated herein by reference. In one embodiment, the protecting group is stable in a basic reaction medium, but can be cleaved by acid. Examples of base-stable, acid-labile protecting groups suitable for use with the invention include, but are not limited to, ethers, such as methyl, methoxy methyl, methylthiomethyl, methoxyethoxymethyl, bis(2 chloroethoxy)methyl, tetrahydropyranyl, tetrahydrothiopyranyl, tetrahyrofuranyl, tetrahydrothiofuranyl, 1-ethoxyethyl, 1-methyl 1-methoxyethyl, tert.-butyl, allyl, benzyl, o-nitrobenzyl, triphenylmethyl, α-naphthyldiphenylmethyl, p-methoxyphenyldiphenylmethyl, 9-(9-phenyl-10-oxo)anthranyl, trimethylsilyl, isopropyldimethylsilyl, tert.-butyldimethylsilyl, tert.-butyldiphenylsilyl, tribenzylsilyl, and triisopropylsilyl; And esters, such as pivaloate, adamantoate, and 2,4,6-trimethylbenzoate.

As used herein and unless otherwise indicated, the term "label" refers to a detectable molecule or atom attached, covalently or non-covalently, to a nucleoside or nucleotide, nucleoside or nucleotide analog, nucleic acid, nucleic acid analog or terminator. In one embodiment, a nucleoside or nucleotide, nucleoside or nucleotide analog, nucleic acid, nucleic acid analog or terminator has a detectable label covalently attached to the nucleobase. The term "label" can also refer to a molecule that modulates detection of another detectable label, such as a quencher. As used herein, the term "detectable label" is intended to include not only a molecule or label which is "directly" detected (e.g., a chromogen or a fluorophore) but also a moiety (e.g., biotin) which is "indirectly" detected by its binding to a second, third, or greater binding partner (e.g., avidin or streptavidin), one of which carries a "direct" label.

Other examples of labels include a fluorescent compound, which, when exposed to light of the proper wavelength, becomes detectable due to fluorescence and is detected and/or measured by microscopy or fluorometry. Commonly used fluorescent labeling compounds include fluorescein isothiocyanate, rhodamine, phycoerythrin, phycocyanin, allophycocyanin, γ-phthalaldehyde and fluorescamine. The detectable label can be a fluorescence-emitting metal such as $^{152}$Eu, or others of the lanthanide series which can be attached to the oligonucleotide using metal chelating groups, such as diethylenetriaminepentaacetic acid or ethylenediaminetetraacetic acid.

The label can be a chemiluminescent compound, the presence of which is detected by measuring luminescence that arises during the course of a chemical reaction. Examples of useful chemiluminescent labeling compounds are luminol, isoluminol, theromatic acridinium ester, imidazole, acridinium salt and oxalate ester. Likewise, a bioluminescent compound can be used to label the oligonucleotide and is detected by measuring luminescence. In this case, a catalytic protein increases the efficiency of the chemiluminescence reaction. Examples of bioluminescent labeling compounds include luciferin, luciferase and aequorin.

As used herein and unless otherwise indicated, the term "fluorescent dye" refers to a fluorescent compound which, when exposed to light, emits energy in the form of fluorescence. "The chromophore of a reporter dye" is the network of atoms of the reporter dye that, when exposed to light, emits radiation at a level that is detectable by conventional spectroscopic means.

A large majority of fluorescent dyes (for example, dyes that contain a sulfonate moiety) are inherently incompatible with the phosphormaidite chemistry used during solid-phase oligonucleotide synthesis. This is due mostly to the instability of these dyes to the chemical conditions present during nucleic acid deprotection and cleavage from the solid-phase where strong bases, such as aqueous ammonia, or primary amines, such as methylamine, are most often used. For instance, sulfonated fluorescent dyes such as Atto490LS (ATTO-TEC, Inc., Siegen, Germany), CF640R, CF680R, (Bio-Techne, Inc., U.S.A.), and Dy380XL, and Dy395XL, Dy396XL (Dyomics, GmbH, Jena, Germany), and JA286 (Roche Molecular Systems, Pleasanton, Calif.) are incompatible with phosphoramidite-based DNA synthesis on the solid-phase support.

As used herein and unless otherwise indicated, the term "non-fluorescent" refers to a compound that, when exposed to radiation, does not emit radiation at a level that is detectable by conventional spectroscopic means.

As used herein and unless otherwise indicated, the term "weakly fluorescent" refers to a compound that, when exposed to radiation, emits radiation at a low level that is detectable by conventional spectroscopic means.

As used herein and unless otherwise indicated, the term "light" refers to electromagnetic energy having a wavelength which causes a reporter dye to fluoresce, wherein that wavelength may be in the range of 190-800 nm.

As used herein and unless otherwise indicated, the term "specific" refers to a nucleic acid used in a reaction, such as a probe used in a hybridization reaction, a primer used in a PCR, or a nucleic acid present in a composition, that hybridizes only with the intended target but not to other nucleic acid molecules in the test sample in the normal testing environment.

As used herein and unless otherwise indicated, the term "selective" refers to a nucleic acid used in a reaction, such as a probe used in a hybridization reaction, a primer used in a PCR, or a nucleic acid present in a pharmaceutical preparation, that hybridizes with the intended target more frequently, more rapidly, or with greater duration than it does with other nucleic acids in the test sample in the normal testing environment.

As used herein, the term "hybridizes under stringent conditions" describes conditions for hybridization and washing under which nucleotide sequences at least 60% (65%, 70%, 75%, or greater) identical to each other typically remain hybridized to each other. Stringent conditions depend on the nature of the nucleic acid (e.g. length, GC content, etc.) and the method itself (hybridization, amplification, etc.). Such methods are well known in the art and can be found in Current Protocols in Molecular Biology, John Wiley & Sons, N.Y. (1989), 6.3.1-6.3.6. In one embodiment, stringent hybridization conditions are hybridization at 6× sodium chloride/sodium citrate (SSC) at about 45° C., followed by one or more washes in 0.1×SSC, 0.2% SDS at about 68° C. In another embodiment, stringent hybridization conditions are hybridization in 6×SSC at about 45° C., followed by one or more washes in 0.2×SSC, 0.1% SDS at 50-65° C. (i.e., one or more washes at 50° C., 55° C., 60° C., or 65° C.). It is understood that the nucleic acids of the invention do not include nucleic acid molecules that hybridize under these conditions solely to a nucleotide sequence consisting of only A or T nucleotides. For example, stringent hybridization of an oligonucleotide of approximately 15-40 bases to a complementary sequence in the polymerase chain reaction (PCR) can be performed under the following conditions: a salt concentration of 50 mM KCl, a buffer concentration of 10 mM Tris-HCl, a $Mg^{2+}$ concentration of 1.5 mM, a pH of 7-7.5 and an annealing temperature of 55-60° C. Moderate stringency hybridization of an oligonucleotide of approximately 15-40 bases to a complementary sequence in the polymerase chain reaction (PCR) can be performed under the following conditions: a salt concentration of 50 mM KCl, a buffer concentration of 10 mM Tris-HCl, a $Mg^{2+}$ concentration of 1.5 mM, a pH of 7-7.5 and an annealing temperature of 48-54° C. Low stringency hybridization of an oligonucleotide of approximately 15-40 bases to a complementary sequence in the polymerase chain reaction (PCR) can be performed under the following conditions: a salt concentration of 50 mM KCl, a buffer concentration of 10 mM Tris-HCl, a $Mg^{2+}$ concentration of 1.5 mM, a pH of 7-7.5 and an annealing temperature of 37-47° C.

As used herein and unless otherwise indicated, the term "stereomerically pure" refers to a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of stereoisomer of the compound and less than about 20% by weight of other stereoisomers the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, a compound that is "pure" or "substantially pure" refers to a composition that comprises one compound and is free of detectable or significant quantities of other compounds. A typical substantially pure composition comprises greater than about 80% by weight of the desired compound and less than about 20% by weight of one or more other compounds, more preferably greater than about 90% by weight of the desired compound and less than about 10% by weight of one or more other compounds, even more preferably greater than about 95% by weight of the desired compound and less than about 5% by weight of one or more other compounds, and most preferably greater than about 97% by weight of the desired compound and less than about 3% by weight of one or more other compounds.

A method of nucleic acid amplification is the Polymerase Chain Reaction (PCR) which is disclosed, among other references, in U.S. Pat. Nos. 4,683,202, 4,683,195, 4,800,159, and 4,965,188. PCR typically employs two or more oligonucleotide primers that bind to a selected nucleic acid template (e.g. DNA or RNA). Primers useful for nucleic acid analysis include oligonucleotides capable of acting as a point of initiation of nucleic acid synthesis within the nucleic acid sequences of the target nucleic acids. A primer can be purified from a restriction digest by conventional methods, or it can be produced synthetically. The primer can be single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90%, or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 5 s to 9 min. In order to not expose the respective polymerase like e.g. the Z05 DNA polymerase to such high temperatures for too long and thus risking a loss of functional enzyme, it can be preferred to use short denaturation steps.

If the double-stranded template nucleic acid is denatured by heat, the reaction mixture is allowed to cool to a temperature that promotes annealing of each primer to its target sequence on the target nucleic acids.

The temperature for annealing can be from about 35° C. to about 70° C., or about 45° C. to about 65° C.; or about 50° C. to about 60° C., or about 55° C. to about 58° C. Annealing times can be from about 10 s to about 1 min. (e.g., about 20 s to about 50 s; about 30 s to about 40 s). In this context, it can be advantageous to use different annealing temperatures in order to increase the inclusivity of the respective assay. In brief, this means that at relatively low annealing temperatures, primers may also bind to targets having single mismatches, so variants of certain sequences can also be amplified. This can be desirable if e.g. a certain organism has known or unknown genetic variants which should also be detected. On the other hand, relatively high annealing temperatures bear the advantage of providing higher specificity, since towards higher temperatures the probability of primer binding to not exactly matching target sequences continuously decreases. In order to benefit from both phenomena, in some embodiments of the invention the process described above comprises annealing at different temperatures, for example first at a lower, then at a higher temperature. If, e.g., a first incubation takes place at 55° C. for about 5 cycles, non-exactly matching target sequences may be (pre-)amplified. This can be followed e.g. by about 45 cycles at 58° C., providing for higher specificity throughout the major part of the experiment. This way, potentially important genetic variants are not missed, while the specificity remains high.

The reaction mixture is then adjusted to a temperature at which the activity of the polymerase is promoted or optimized, i.e., a temperature sufficient for extension to occur from the annealed primer to generate products complementary to the nucleic acid to be analyzed. The temperature should be sufficient to synthesize an extension product from each primer that is annealed to a nucleic acid template, but should not be so high as to denature an extension product from its complementary template (e.g., the temperature for extension generally ranges from about 40° to 80° C. (e.g., about 50° C. to about 70° C.; about 65° C.). Extension times can be from about 10 s to about 5 min., or about 15 s to 2 min., or about 20 s to about 1 min., or about 25 s to about 35 s. The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acids. The limiting factors in the reaction are the amounts of primers, thermostable enzyme, and nucleoside triphosphates present in the reaction. The cycling steps (i.e., denaturation, annealing, and extension) can be repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

PCR can be carried out in which the steps of annealing and extension are performed in the same step (one-step PCR) or, as described above, in separate steps (two-step PCR). Performing annealing and extension together and thus under the same physical and chemical conditions, with a suitable enzyme such as, for example, the Z05 DNA polymerase, bears the advantage of saving the time for an additional step in each cycle, and also abolishing the need for an additional temperature adjustment between annealing and extension. Thus, the one-step PCR reduces the overall complexity of the respective assay.

In general, shorter times for the overall amplification can be preferred, as the time-to-result is reduced and leads to a possible earlier diagnosis.

Other nucleic acid amplification methods to be used comprise the Ligase Chain Reaction [LCR; Wu D. Y. and Wallace R. B., Genomics 4 (1989) 560-69; and Barany F., Proc. Natl. Acad. Sci. USA 88 (1991) 189-193]; Polymerase Ligase Chain Reaction (Barany F., PCR Methods and Applic. 1 (1991) 5-16); Gap-LCR (WO 90/01069); Repair Chain Reaction (EP 0439182 A2), 3SR (Kwoh D. Y. et al., Proc. Natl. Acad. Sci. USA 86 (1989) 1173-1177; Guatelli J. C. et al., Proc. Natl. Acad. Sci. USA 87 (1990) 1874-1878; WO 92/08808), and NASBA (U.S. Pat. No. 5,130,238). Further, there are strand displacement amplification (SDA), transcription mediated amplification (TMA), and Qb-amplification (for a review see e.g. Whelen A. C. and Persing D. H., Annu. Rev. Microbiol. 50 (1996) 349-373; Abramson R. D. and Myers T. W., Curr. Opin. Biotechnol. 4 (1993) 41-47).

The term "Cp value" or "crossing point" value refers to a value that allows quantification of input target nucleic acids. The Cp value can be determined according to the second-derivative maximum method (Van Luu—The et al., "Improved real-time RT-PCR method for high-throughput measurements using second derivative calculation and double correction", BioTechniques, Vol. 38, No. 2, February 2005, pp. 287-293). In the second derivative method, a Cp corresponds to the first peak of a second derivative curve. This peak corresponds to the beginning of a log-linear phase. The second derivative method calculates a second derivative value of the real-time fluorescence intensity curve, and only one value is obtained. The original Cp method is based on a locally defined, differentiable approximation of the intensity values, e.g., by a polynomial function. Then the third derivative is computed. The Cp value is the smallest root of the third derivative. The Cp can also be determined using the fit point method, in which the Cp is determined by the intersection of a parallel to the threshold line in the log-linear region. The Cp value provided by the LightCycler instrument offered by Roche by calculation according to the second-derivative maximum method.

The term "PCR efficiency" refers to an indication of cycle to cycle amplification efficiency. PCR efficiency is calculated for each condition using the equation: % PCR efficiency ($10^{(-slope)}-1)\times 100$, wherein the slope was calculated by linear regression with the log copy number plotted on the y-axis and Cp plotted on the x-axis. PCR efficiency can be measured using a perfectly matched or mismatched primer template.

The term "FRET" or "fluorescence resonance energy transfer" or "Förster resonance energy transfer" refers to a transfer of energy between at least two chromophores, a donor chromophore and an acceptor chromophore (referred to as a quencher). The donor typically transfers the energy to the acceptor when the donor is excited by light radiation with a suitable wavelength. The acceptor typically re-emits the transferred energy in the form of light radiation with a different wavelength. When the acceptor is a "dark" quencher, it dissipates the transferred energy in a form other than light. Whether a particular fluorophore acts as a donor or an acceptor depends on the properties of the other member of the FRET pair. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Calif.), Iowa Black™ (Integrated DNA Tech., Inc., Coralville, Iowa), and BlackBerry™ Quencher 650 (BBQ-650) (Berry & Assoc., Dexter, Mich.).

The methods set out above can be based on FRET between a donor fluorescent moiety and an acceptor fluorescent moiety. A representative donor fluorescent moiety is fluorescein, and representative corresponding acceptor fluorescent moieties include LC-Red 640, LC-Red 705, Cy5, and Cy5.5. Typically, detection includes exciting the sample at a wavelength absorbed by the donor fluorescent moiety and visualizing and/or measuring the wavelength emitted by the corresponding acceptor fluorescent moiety. In the process according to the invention, detection can be followed by quantitating the FRET. For example, detection is performed after each cycling step. For example, detection is performed in real time. By using commercially available real-time PCR instrumentation (e.g., LightCycler™ or TaqMan®), PCR amplification and detection of the amplification product can be combined in a single closed cuvette with significantly reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory.

The following patent applications describe real-time PCR as used in the LightCycler® technology: WO 97/46707, WO 97/46714 and WO 97/46712. The LightCycler® instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the thermal chamber.

TagMan® technology utilizes a single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. Typical fluorescent dyes used in this format are for example, among others, FAM, HEX, Cy5, JA270, Cyan and Cy5.5. During the annealing step of the PCR reaction, the labeled hybridization probe binds to the target nucleic acid (i.e., the amplification product) and is degraded by the 5' to 3' exonuclease activity of the Taq or another suitable polymerase as known by the skilled artisan, such as a mutant Z05 polymerase, during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected.

In both detection formats described above, the intensity of the emitted signal can be correlated with the number of original target nucleic acid molecules.

Recently, methods using "tagged" TagMan® probes for performing multiplexed PCR assays have been described in U.S. Patent Publication No. 2018/0073056 and U.S. Patent Publication No. 2018/0073064, both incorporated by reference herein in their entireties.

As an alternative to FRET, an amplification product can be detected using a double-stranded DNA binding dye such as a fluorescent DNA binding dye [e.g., SYBRGREEN I® or SYBRGOLD® (Molecular Probes, Inc., Eugene, Oreg.)]. Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

Molecular beacons in conjunction with FRET can also be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g. a hairpin). As a result of secondary structure formation within the probe, both fluorescent moieties are in spatial proximity when the probe is in solution. After hybridization to the amplification products, the secondary structure of the probe is disrupted and the fluorescent moieties become separated from one another such that after excitation with light of a suitable wavelength, the emission of the first fluorescent moiety can be detected.

Thus, a method according to the invention is the method described above using FRET, wherein said probes comprise a nucleic acid sequence that permits secondary structure formation, wherein said secondary structure formation results in spatial proximity between said first and second fluorescent moiety.

Efficient FRET can only take place when the fluorescent moieties are in direct local proximity and when the emission spectrum of the donor fluorescent moiety overlaps with the absorption spectrum of the acceptor fluorescent moiety.

Thus, in an embodiment, said donor and acceptor fluorescent moieties are within no more than five nucleotides of each other on said probe. In a further embodiment, said acceptor fluorescent moiety is a quencher.

As described above, in the TagMan® format, during the annealing step of the PCR reaction, the labeled hybridization probe binds to the target nucleic acid (i.e., the amplification product) and is degraded by the 5'- to 3'-exonuclease activity of the Taq or another suitable polymerase as known by the skilled artisan, such as a mutant Z05 polymerase, during the subsequent elongation phase. Thus, in an embodiment, in the process described above, amplification employs a polymerase enzyme having 5'- to 3'-exonuclease activity.

It is further advantageous to carefully select the length of the amplicon that is yielded as a result of the process described above. Generally, relatively short amplicons increase the efficiency of the amplification reaction. Thus, an aspect of the invention is the process described above, wherein the amplified fragments comprise up to 450 bases, up to 300 bases, up to 200 bases, or up to 150 bases.

A "sequence" is the primary structure of a nucleic acid, i.e. the specific arrangement of the single nucleobases of which the respective nucleic acids consists. It has to be understood that the term "sequence" does not denote a specific type of nucleic acid such as RNA or DNA, but applies to both as well as to other types of nucleic acids such as e.g. PNA or others. Where nucleobases correspond to each other, particularly in the case of uracil (present in RNA) and thymine (present in DNA), these bases can be considered equivalent between RNA and DNA sequences, as well-known in the pertinent art.

Clinically relevant nucleic acids are often DNA which can be derived e.g. from DNA viruses like e.g. Hepatitis B Virus (HBV), Cytomegalovirus (CMV) and others, or bacteria like e.g. *Chlamydia trachomatis* (CT), *Neisseria gonorrhoeae* (NG) and others. In such cases, it can be advantageous to use an internal control nucleic acid consisting of DNA, in order to reflect the target nucleic acids properties. The terms "cell", "cell line", and "cell culture" can be used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants. The cells can be prokaryotic or eukaryotic.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, positive retroregulatory elements (see U.S. Pat. No. 4,666,848, incorporated herein by reference), and possibly other sequences. Eucaryotic cells are known to utilize promoters, polyadenylation signals, and enhancers.

The term "operably linked" refers to the positioning of the coding sequence such that control sequences will function to drive expression of the protein encoded by the coding sequence. Thus, a coding sequence "operably linked" to control sequences refers to a configuration wherein the coding sequences can be expressed under the direction of a control sequence.

The terms "restriction endonucleases" and "restriction enzymes" refer to enzymes, typically bacterial in origin, which cut double-stranded DNA at or near a specific nucleotide sequence.

Families of amino acid residues having similar side chains are defined herein. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine), nonpolar side chains (e.g., alanine, valine, leucine, isoleucine, proline, phenylalanine, methionine, tryptophan, cysteine, glycine), beta-branched side chains (e.g., threonine, valine, isoleucine) and aromatic side chains (e.g., tyrosine, phenylalanine, tryptophan, histidine).

The term "reagent solution" is any solution containing at least one reagent needed or used for PCR purposes. Most typical ingredients are polymerase, nucleotide, primer, ions, magnesium, salts, pH buffering agents, nucleoside triphosphates (NTPs) or deoxyribonucleoside triphosphates (dNTPs), probe, fluorescent dye (may be attached to probe), nucleic acid binding agent, a nucleic acid template. The reagent may also be another polymerase reaction additive, which has an influence on the polymerase reaction or its monitoring.

The term "mastermix" refers to a mixture of all or most of the ingredients or factors necessary for PCR to occur, and in some cases, all except for the template and primers which are sample and amplicon specific. Commercially available mastermixes are usually concentrated solutions. A mastermix may contain all the reagents common to multiple samples, but it may also be constructed for one sample only. Using mastermixes helps to reduce pipetting errors and variations between samples due to differences between pipetted volumes.

The term "thermostable polymerase" refers to an enzyme that is stable to heat, is heat resistant and retains sufficient activity to effect subsequent primer extension reactions after being subjected to the elevated temperatures for the time necessary to denature double-stranded nucleic acids. Generally, the synthesis is initiated at the 3' end of each primer and proceeds in the 5' to 3' direction along the template strand. Heating conditions necessary for nucleic acid denaturation are well known in the art and are exemplified in U.S. Pat. Nos. 4,965,188 and 4,889,818, which are incorporated herein by reference. As used herein, a thermostable polymerase is suitable for use in a temperature cycling reaction such as PCR. The examples of thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, and the like. Nonetheless, polymerases that are not thermostable also can be employed in PCR assays provided the enzyme is replenished.

A "polymerase with reverse transcriptase activity" is a nucleic acid polymerase capable of synthesizing DNA based on an RNA template. It is also capable of replicating a single or double-stranded DNA once the RNA has been reverse transcribed into a single strand cDNA. In an embodiment of the invention, the polymerase with reverse transcriptase activity is thermostable.

In the amplification of an RNA molecule by a DNA polymerase, the first extension reaction is reverse transcription using an RNA template, and a DNA strand is produced. The second extension reaction, using the DNA template, produces a double-stranded DNA molecule. Thus, synthesis of a complementary DNA strand from an RNA template by a DNA polymerase provides the starting material for amplification.

Thermostable DNA polymerases can be used in a coupled, one-enzyme reverse transcription/amplification reaction. The term "homogeneous", in this context, refers to a two-step single addition reaction for reverse transcription and amplification of an RNA target. By homogeneous it is meant that following the reverse transcription (RT) step, there is no need to open the reaction vessel or otherwise adjust reaction components prior to the amplification step.

In a non-homogeneous RT-PCR reaction, following reverse transcription and prior to amplification one or more of the reaction components such as the amplification reagents are e.g. adjusted, added, or diluted, for which the reaction vessel has to be opened, or at least its contents have to be manipulated. Both homogeneous and non-homogeneous embodiments are comprised by the scope of the invention.

Reverse transcription is a fundamental step in an RT-PCR. It is, for example, known in the art that RNA templates show a tendency towards the formation of secondary structures that may hamper primer binding and/or elongation of the cDNA strand by the respective reverse transcriptase. Thus, relatively high temperatures for an RT reaction are advantageous with respect to efficiency of the transcription. On the other hand, raising the incubation temperature also implies higher specificity, i.e. the RT primers will not anneal to sequences that exhibit mismatches to the expected sequence or sequences. Particularly in the case of multiple different target RNAs, it can be desirable to also transcribe and subsequently amplify and detect sequences with single mismatches, e.g. in the case of the possible presence of unknown or rare substrains or subspecies of organisms in the fluid sample.

In order to benefit from both advantages described above, i.e. the reduction of secondary structures and the reverse transcription of templates with mismatches, the RT incubation can be carried out at more than one different temperature.

Therefore, an aspect of the invention is the process described above, wherein said incubation of the polymerase with reverse transcriptase activity is carried out at different temperatures from 30° C. to 75° C., or from 45° C. to 70° C., or from 55° C. to 65° C.

As a further important aspect of reverse transcription, long RT steps can damage the DNA templates that may be present in the fluid sample. If the fluid sample contains both RNA and DNA species, it is thus favorable to keep the duration of the RT steps as short as possible, but at the same time ensuring the synthesis of sufficient amounts of cDNA for the subsequent amplification and optional detection of amplificates.

Thus, an aspect of the invention is the process described above, wherein the period of time for incubation of the polymerase with reverse transcriptase activity is up to 30 min., 20 min., 15 min., 12.5 min., 10 min., 5 min., or 1 min.

A further aspect of the invention is the process described above, wherein the polymerase with reverse transcriptase activity and comprising a mutation is selected from the group consisting of
  a) a CS5 DNA polymerase
  b) a CS6 DNA polymerase
  c) a *Thermotoga maritima* DNA polymerase
  d) a *Thermus aquaticus* DNA polymerase
  e) a *Thermus thermophilus* DNA polymerase
  f) a *Thermus flavus* DNA polymerase
  g) a *Thermus filiformis* DNA polymerase
  h) a *Thermus* sp. sps17 DNA polymerase
  i) a *Thermus* sp. Z05 DNA polymerase
  j) a *Thermotoga neapolitana* DNA polymerase
  k) a *Termosipho africanus* DNA polymerase
  l) a *Thermus caldophilus* DNA polymerase Particularly suitable for these requirements are enzymes carrying a mutation in the polymerase domain that enhances their reverse transcription efficiency in terms of a faster extension rate.

Therefore, in the process described above, wherein the polymerase with reverse transcriptase activity is a polymerase comprising a mutation conferring an improved nucleic acid extension rate and/or an improved reverse transcriptase activity relative to the respective wildtype polymerase.

In an embodiment, in the process described above, the polymerase with reverse transcriptase activity is a polymerase comprising a mutation conferring an improved reverse transcriptase activity relative to the respective wild-type polymerase.

Polymerases carrying point mutations that render them particularly useful are disclosed in WO 2008/046612. In particular, polymerases to be used can be mutated DNA polymerases comprising at least the following motif in the polymerase domain:

T-G-R-L-S-S-Xb7-Xb8-P-N-L-Q-N; wherein Xb7 is an amino acid selected from S or T and wherein Xb8 is an amino acid selected from G, T, R, K, or L, wherein the polymerase comprises 3' to 5' exonuclease activity and has an improved nucleic acid extension rate and/or an improved reverse transcription efficiency relative to the wildtype DNA polymerase, wherein in said wildtype DNA polymerase Xb8 is an amino acid selected from D, E or N.

One example is mutants of the thermostable DNA polymerase from *Thermus* species Z05 (described e.g. in U.S. Pat. No. 5,455,170), said variations comprising mutations in the polymerase domain as compared with the respective wildtype enzyme Z05. An embodiment for the method according to the invention is a mutant Z05 DNA polymerase wherein the amino acid at position 580 is selected from the group consisting of G, T, R, K and L. Other examples of mutant Z05 DNA polymerases that have improved reverse transcription efficiency include but are not limited to the D580G, E522G mutant described in U.S. Pat. No. 9,090,883; the D580G, I709K mutant described in U.S. Pat. No. 9,017,979; the D580G, I709K, 1640F mutant described in U.S. Pat. No. 8,759,063; the D580G, I709K, 1616M mutant described in U.S. Pat. No. 8,945,882; and the D580G, I709K, Y698F mutant described in U.S. Pat. No. 9,080,156 (all incorporated herein by reference).

For reverse transcription using a thermostable polymerase, a divalent cation such as $Mn^{2+}$ or $Mg^{2+}$ is typically included as a salt, for example, manganese chloride ($MnCl_2$), manganese acetate [$Mn(OAc)_2$], or manganese sulfate ($MnSO_4$) or magnesium chloride ($MgCl_2$), magnesium acetate [$Mg(OAc)_2$], or magnesium sulfate ($MgSO_4$). If $MnCl_2$ is included in a reaction containing 50 mM Tricine buffer, for example, the $MnCl_2$ is generally present at a concentration of 0.5-7.0 mM; 2.5-3.5 mM is generally present when 200 μM of each dGTP, dATP, dUTP, and, dCTP are utilized.

A "modified" thermostable polymerase refers to a polymerase in which at least one monomer differs from the reference sequence, such as a native or wild-type form of the polymerase or another modified form of the polymerase. Exemplary modifications include monomer insertions, deletions, and substitutions. Modified polymerases also include chimeric polymerases that have identifiable component sequences (e.g., structural or functional domains, etc.) derived from two or more parents. Also included within the definition of modified polymerases are those comprising chemical modifications of the reference sequence. Further examples of modified thermostable polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, Z05 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "thermoactive polymerase" refers to an enzyme that is active at the elevated temperatures necessary to ensure specific priming and primer extension (e.g., 55-80° C.).

The terms "peptide," "polypeptide," and "protein" are used interchangeably. The terms "nucleic acid", "oligonucleotide", and "polynucleotide" are used interchangeably. Amino acid sequences are written from amino terminus to carboxy terminus, unless otherwise indicated. Single-stranded nucleic acid sequences are written 5' to 3', unless otherwise indicated. The top strand of a double-stranded nucleic acid sequence is written 5' to 3', and the bottom strand is written 3' to 5', unless otherwise indicated.

While the foregoing invention has been described in some detail for purposes of clarity and understanding, it will be clear to one skilled in the art from a reading of this disclosure that various changes in form and detail can be made without departing from the true scope of the invention. For example, all the compositions and methods described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The following examples are given to illustrate embodiments of the present invention as it is presently preferred to practice. It will be understood that the examples are illustrative, and that the invention is not be considered as restricted except as indicated in the appended claims.

EXAMPLES

Abbreviations: dATP=2'-deoxyadenosine 5'-triphosphate, dCTP=2'-deoxycytidine 5'-triphosphate, DEPC=diethyl pyrocarbonate, dGTP=2'-deoxyguanosine 5'-triphosphate, DIPEA=N,N-diisopropylethylamine, DMF=N,N'-dimethylformamide, DMSO=dimethyl sulfoxide, DMT-MM=4-(4,6-dimethoxy-1,3,5-triazin-2-yl)-4-methylmorpholinium salt, dUTP=2'-deoxyuridine 5'-triphosphate, eq.=equivalents, HEPBS=N-(2-hydroxyethyl) piperazine-N'-(4-butanesulfonic acid), HEPPS=4-(2-hydroxyethyl)-1-piperazinepropanesulfonic acid, LNA=Locked nucleic acid, MeCN=acetonitrile, NHS=N-hydroxysuccinimide, NMP=1-methyl-2-pyrrolidinone, qPCR=real-time polymerase chain reaction, RT=room temperature, TEAA=triethylammonium acetate, TEAB=triethylammonium bicarbonate, Tris.HCl=tris(hydroxymethyl)aminomethane hydrochloride, UPLC-MS=ultra-performance liquid chromatography coupled to a mass spectrometer.

General Materials and Methods: DNA oligonucleotides and DNA/LNA hybrid oligonucleotides carrying a primary amino-modification were synthesized by solid-phase DNA synthesis using an amino-modifier phosphoramidite. For 5'-terminal modifications 6-(trifluoroacetylamino)-hexyl-(2-cyanoethyl)-(N,N-diisopropyl)-phosphoramidite was used. For internal modifications 5'-dimethoxytrityl-5-[N-(trifluoroacetylaminohexyl)-3-acrylimido]-2'-deoxyuridine, 3'-[(2-cyanoethyl)-(N,N-diisopropyl)]-phosphoramidite was used. All DNA sequences contained a 3'- or 5'-BHQ-2 (Black Hole Quencher®) and a 3'-phosphate if BHQ-2 was at the 5'-end. Water was of ultra-high purity with a resistivity of at least 18.2 MΩ·cm at 25° C. All components for quantitative PCR (qPCR) were prepared with water that was treated with DEPC.

Example 1: DNA Labeling with Fluorescent Dyes

DNA pretreatment: The unpurified DNA oligonucleotide (crude) obtained from standard solid-phase DNA synthesis was deprotected and desalted with standard methods to remove any traces of residual amines. The oligonucleotide (1.0 μmol synthesis scale) was lyophilized and redissolved in water (100 μL) with the aid of a warm water bath. An aqueous solution of lithium chloride (80 μL, 10.0 M) was added and the mixture was shaken vigorously for 10.0 min. Ice-cold ethanol (3.3 mL) was added and the tube was gently inverted several times. The mixture was cooled for 20 min at −20° C. and centrifuged (2500 rpm) in a pre-cooled centrifuge for 30 min. at 7° C. The colorless supernatant was carefully decanted and discarded. The remaining solid was washed with dry ethanol, dried at high vacuum, and redissolved in aqueous buffer (1.0 mL, 50 mM, pH 8.0-9.0). The buffer was selected from borate, carbonate, HEPBS, HEPPS, or TEAB. An analytical quantity of the DNA was analyzed with UPLC to determine the amount of the amino-modified target sequence. The total nucleic acid concentration was determined with a spectrophotometer, using the calculated extinction coefficient of the target DNA sequence at 260 nm.

Preactivation: The fluorescent dyes Atto490LS (ATTO-TEC, Inc., Siegen, Germany), CF640R, CF680R, (Bio-Techne, Inc., U.S.A.), Chromeo™ 494 (Active Motif, Inc., Carlsbad, Calif.), Coumarin 343 (C343), Dy380XL, Dy395XL, Dy396XL (Dyomics GmbH, Jena, Germany), and JA286 (Roche Molecular Systems, Pleasanton, Calif.) were obtained as carboxylic acids and used without further manipulation. In a glass vial the fluorescent dye (1.0 eq. carboxylic acid) was dissolved in dry organic solvent (20 mM). Depending on the solubility of the label, the solvent was selected from DMSO, NMP, DMF, or a 50% mixture thereof with water. For labeling reactions that required less than 1.0 mg of carboxylic acid, the concentration was adjusted by absorption spectroscopy using the extinction coefficient of the chromophore. DIPEA (1.2 eq.) or another weak non-nucleophilic base was added and the solution was briefly mixed. In a separate reaction vial the tetrafluoroborate salt of DMT-MM (2.0 eq.) was weighed in, the carboxylic acid solution was added, followed by vigorous mixing until all solids were dissolved. The preactivation was carried out on the Thermoshaker for 15 min. at RT.

Labeling reaction: The preactivation solution (75 μL, 3.0 eq.) was quickly mixed with the DNA solution (100 μL, 1.0 eq. primary amine) and the labeling reaction was carried out on a Thermoshaker at RT. The progress of the reaction was monitored by UPLC analysis, for which a sample of the reaction mixture (1.0 μL) was diluted with water (19.0 μL) prior to UPLC injection (7.0 μL). When UPLC analysis indicated that the reaction was complete, the solution was diluted tenfold with TEAA buffer (100 mM, pH 7.0), or Tris-HCl buffer (50.0 mM, pH 7.5), and stored frozen until purification. Results of the UPLC analyses are shown in FIG. 2-FIG. 5.

Figure 6:
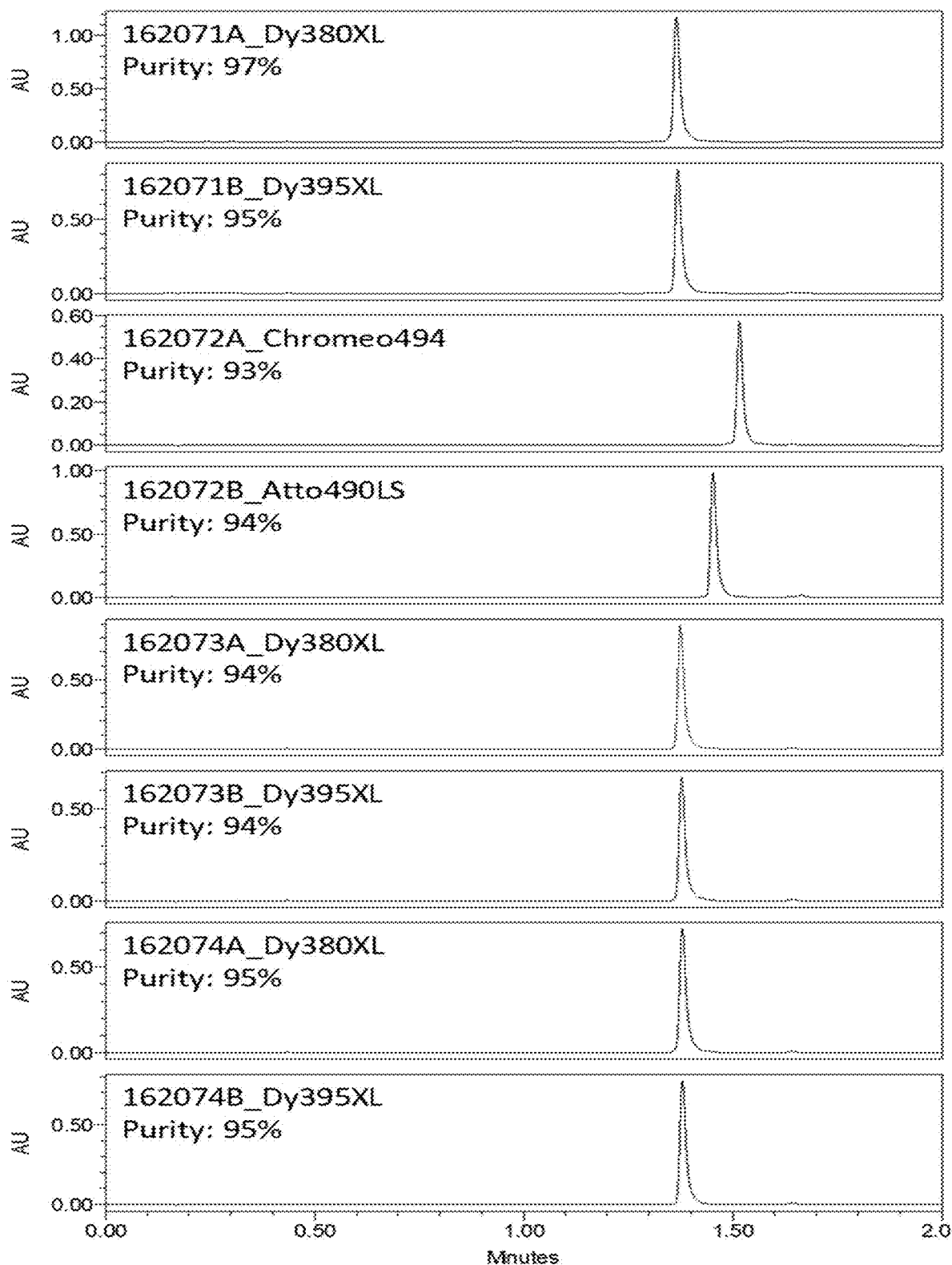
FIG. 6 shows the final UPLC analysis of DNA oligonucleotide probes as obtained by the labeling reaction with fluorescent dyes using DMT-MM and subsequent purification. The lengths of the DNA oligonucleotide sequences were 30mer (162071), 29mer (162072), and 33mer (162073, 162074), each containing a 3'-BHQ-2 quencher.
Figure 7A:
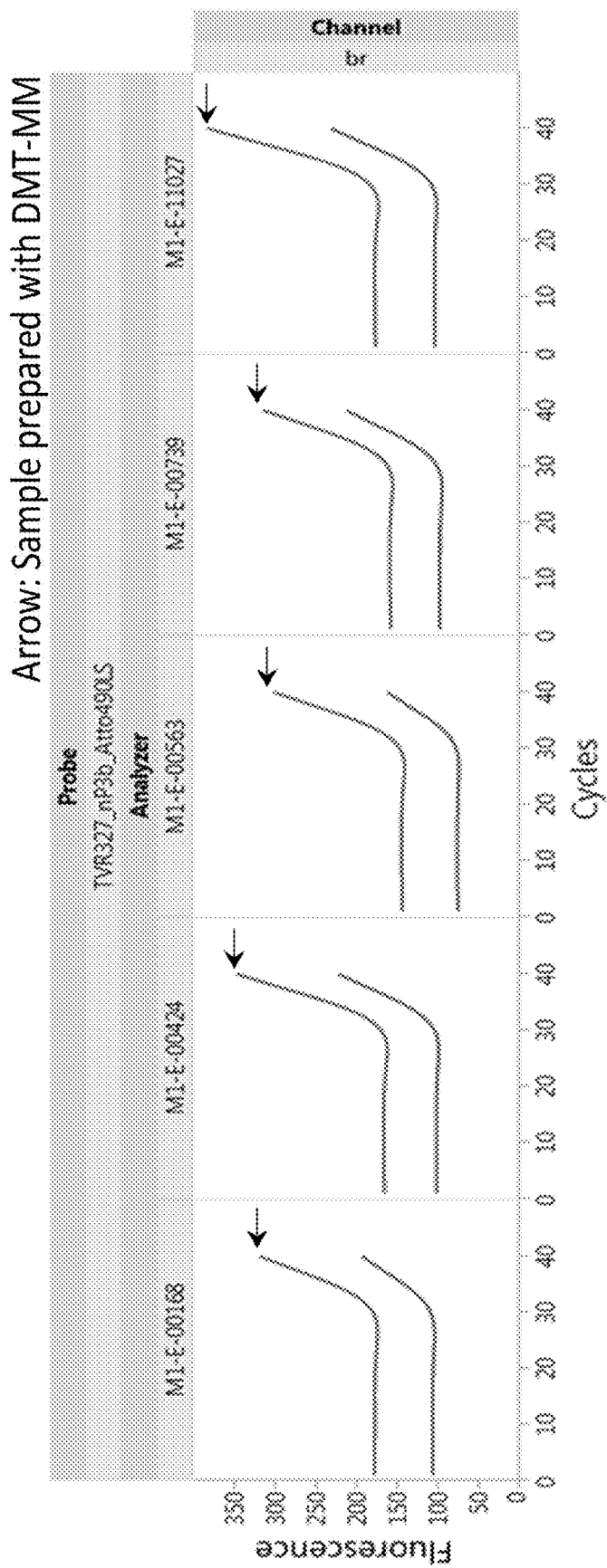
FIG. 7A, FIG. 7B, FIG. 7C, FIG. 7D show the growth curves generated from the quantitative PCR (qPCR) experiments described in Example 2. The arrows show the curves from DNA probes labeled with DMT-MM.
Figure 7B:
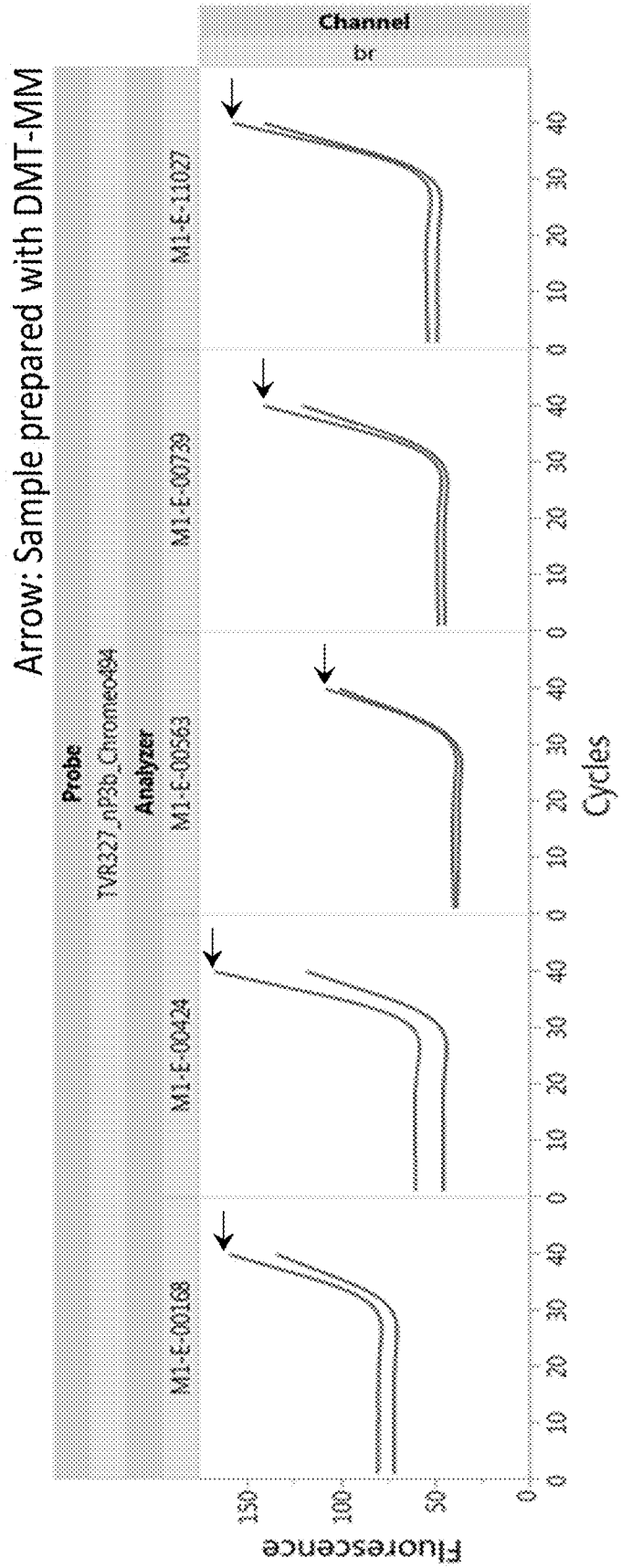
Figure 7C:
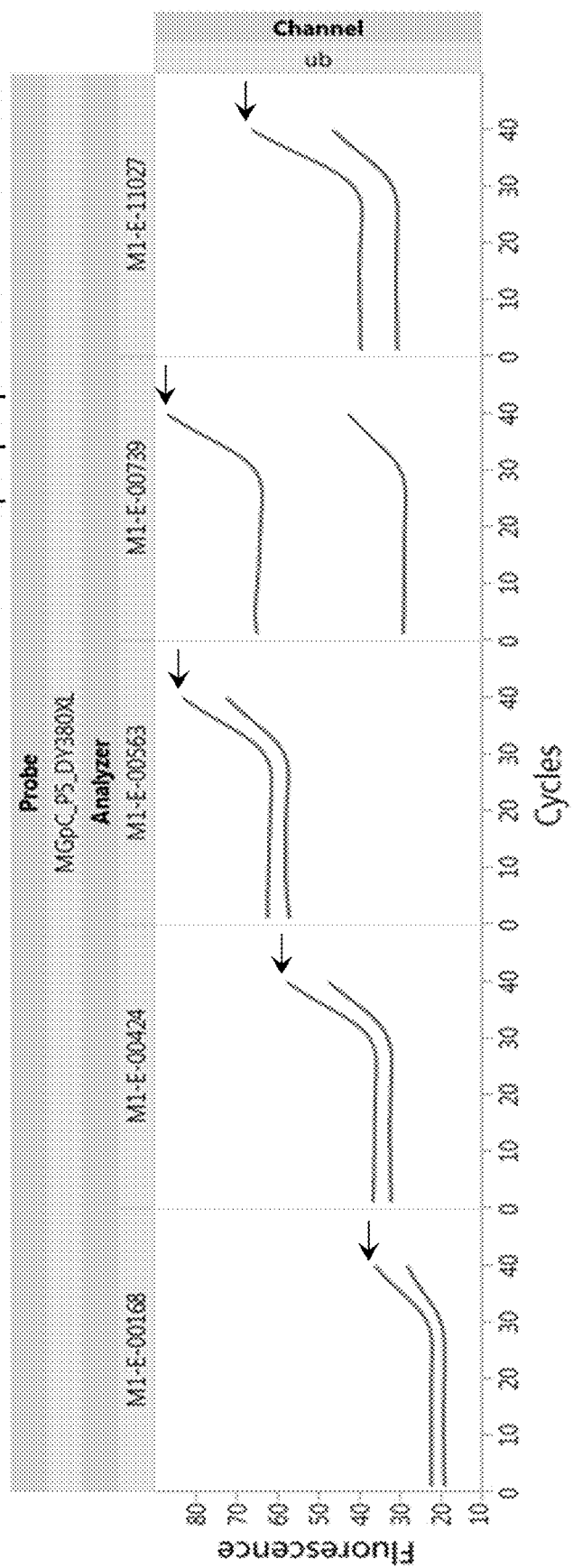
Figure 7D:
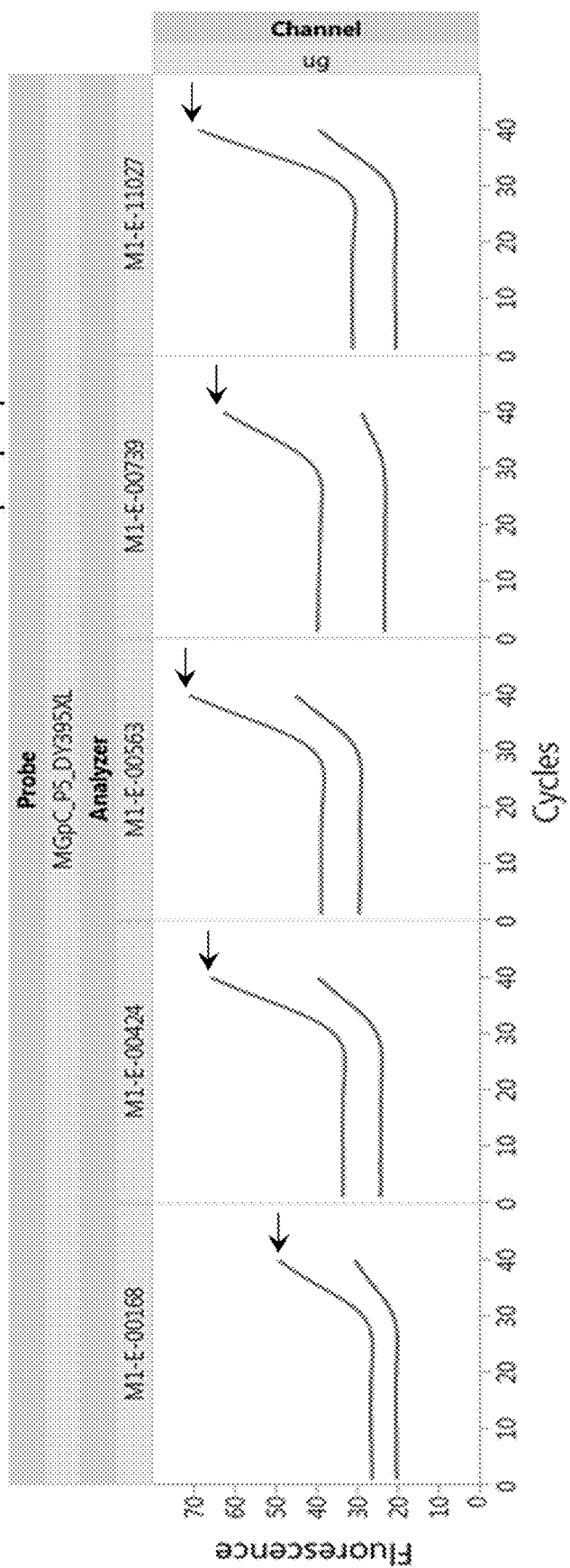

Purification: The labeled DNA was purified with reversed-phase liquid chromatography using Tris-HCl (50.0 mM, pH 7.5) or TEAA (0.1 mM, pH 7.0) and MeCN with results shown in FIG. 6. The combined product fractions were concentrated on a centrifugal vacuum concentrator and desalted by size-exclusion chromatography. The purified DNA probes (0.1 mM) were lyophilized and redissolved in TE buffer (10.0 mM Tris-HCl, 1.0 mM EDTA) for qPCR.

Example 2: qPCR Performance of DNA Probes

The quality and functionality of DNA probes was addressed by direct comparison of the qPCR performance of probes that were prepared with DMT-MM reagent and probes that were prepared with traditional NHS ester chemistry. qPCR was conducted on Roche Cobas® LIAT® systems. Target DNA sequences were based on the *Trichomonas vaginalis* and *Mycoplasma genitalium* pathogens.

The following qPCR mixtures were prepared at multifold volumes to allow singleplex reactions with several replicates. The master mixture contained tricine buffer (30 mM, pH 8.7), potassium acetate (40.0 mM), DMSO [1.08% (v/v)], EDTA (20 μM), Tween® 20 [0.02% (w/v)], sodium azide [0.09% (w/v)], dATP (0.4 mM), dCTP (0.4 mM), dGTP (0.4 mM), and dUTP (0.4 mM), forward and reverse primers (1.0 μM each), and DNA probe (0.1 μM). The cofactor mixture contained magnesium sulfate (1.0 M), and sodium azide [10% (w/v)]. The enzyme mixture contained tricine buffer (0.28 M, pH 8.75), potassium acetate (0.280 M), sodium azide [0.09% (w/v)], EDTA (155.0 DMSO [7.56% (v/v)], glycerol [7.015% (v/v)], aptamer NTQ-46A (2.8 polymerase (5.4 U/μL), and uracil-DNA glycosylase (1.3 U/μL). The elution buffer contained Tris.HCl, bovine serum albumin [1.25 mg/mL (w/v)], and sodium azide [0.09% (w/v)].

Cobas® LIAT® sample tubes were filled with master mixture (10 segment 10), cofactor mixture (10 segment 9), enzyme mixture (10 segment 8), and elution buffer containing the qPCR target (40 segment 7). The target DNA was added to segment 7. qPCR was conducted with five cycles of denaturation at (95° C., 3 s), annealing at (61° C., 1 s), and extension at (62° C., 3 s). Consecutive cycles were performed with denaturation at (93° C., 2 s), annealing at (61° C., 1 s), and extension at (62° C., 3 s). For each DNA probe five replicates were run on five Cobas® LIAT® system units.

Result: As can be seen in FIG. 7A, FIG. 7B, FIG. 7C, FIG. 7D and FIG. 8, DNA probes labeled by in situ activation with DMT-MM showed higher baseline fluorescence intensity and an improved $K_{exp}$ coefficient, indicating a more robust qPCR. In conclusion DNA probes prepared by in situ activation with DMT-MM showed comparable or better performance.

Example 3: Large-Scale Labeling of DNA with Fluorescent Dyes

The DNA oligonucleotide starting material was obtained from standard solid-phase synthesis on the 15.0 µmol scale and used for the labeling reaction without purification.

DNA pretreatment: The crude DNA oligonucleotide was desalted, lyophilized, and redissolved in water (1.0 mL) with the aid of a warm water bath. Dry sodium iodide was added to a final concentration of 10.0 M, ensuring that the salt was completely dissolved. The mixture was diluted with ethanol (200 proof, 30.0 mL), briefly vortexed, and then kept at 15 min. at room temperature (RT). The formed precipitate was isolated by centrifugation (4000 rpm, 5.0 min.) at RT. After decanting the supernatant, the solid precipitate was thoroughly washed with ethanol (2×10.0 mL) and subsequently dried at high vacuum. For the labeling reaction, the DNA oligonucleotide was redissolved in TEAB buffer (0.1 M, pH 8.5) and an analytical quantity was analyzed with UPLC to determine the amount of the amino-modified target sequence. The total nucleic acid concentration was determined with a spectrophotometer, using the calculated extinction coefficient of the target sequence at 260 nm.

Preactivation: The fluorescent dye (1.0 eq. carboxylic acid) was dissolved in dry DMSO (6.0 mM). DIPEA (1.1 eq.) was added and the solution was briefly mixed. In a glass vial DMT-MINI tetrafluoroborate (2.0 eq.) was weighed in and added at once to the carboxylic acid solution, followed by mixing until all solids were dissolved. The preactivation was carried out on the Thermoshaker for 15 min. at RT.

Labeling reaction: The preactivation solution (3.0 eq. carboxylic acid) was quickly added to a stirring solution of the DNA starting material (1.0 eq. primary amine) in a conical reaction vial. The concentration of organic solvent was 40% and the final DNA concentration of the target sequence was between 1.5 and 1.7 mM, dependent on the purity of the crude DNA. The labeling reaction was kept stirring for 20 min. at RT, analyzed by UPLC, and diluted tenfold with TEAA buffer (100 mM, pH 7.0) for subsequent purification.

Purification: The labeled DNA was purified with reversed-phase liquid chromatography with TEAA (0.1 mM, pH 7.0) and MeCN. The combined product fractions were desalted by solid-phase extraction ($C_{18}$), lyophilized to dryness, and redissolved in TE buffer (10.0 mM Tris.HCl, 1.0 mM EDTA) for qPCR.

Figure 9A:
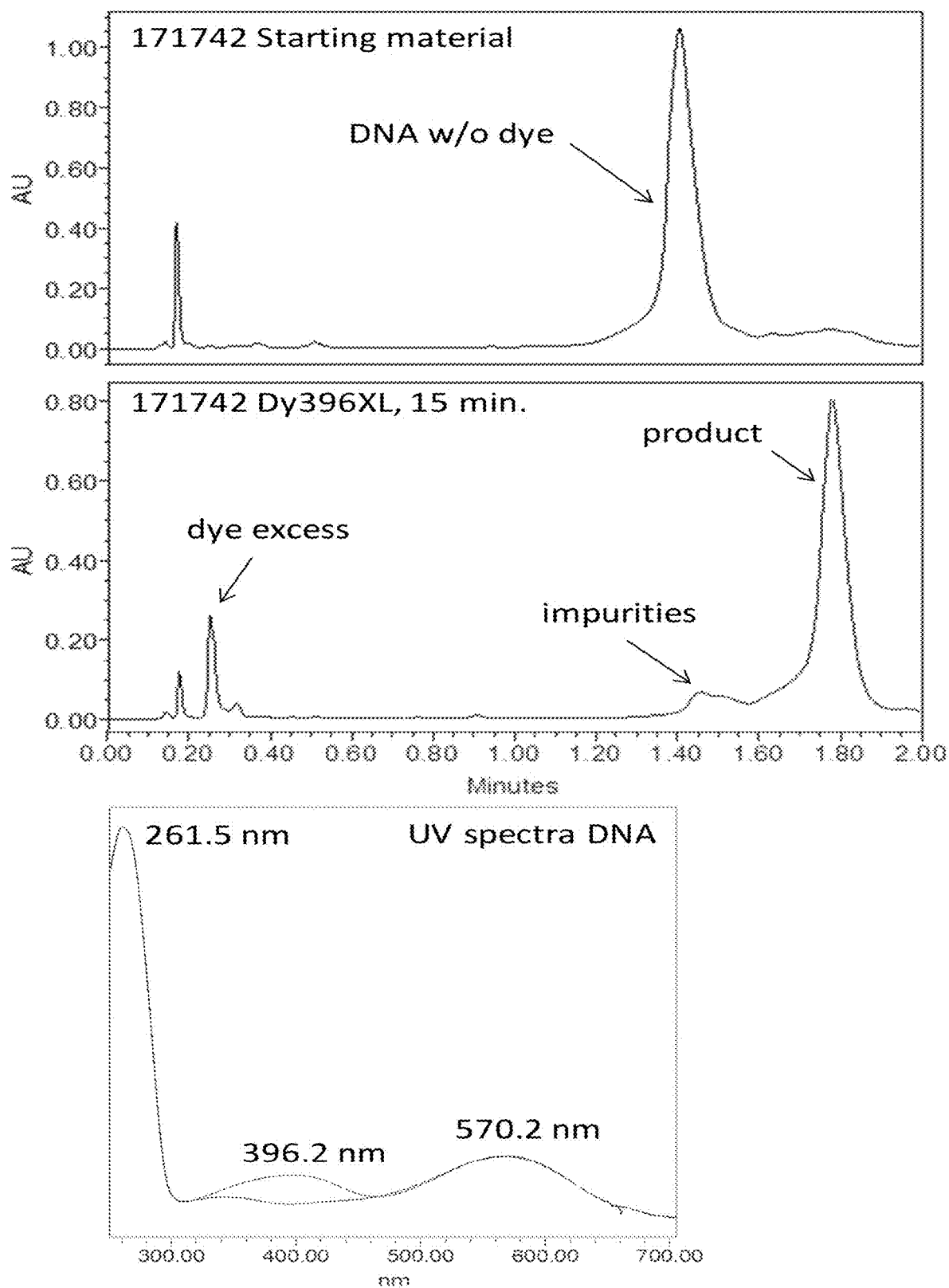
FIG. 9A shows a representative example for a large-scale labeling reaction using DMT-MM as described in Example 3. The 33mer oligonucleotide (171742) with a 3'-BHQ-2 quencher was obtained from a solid-phase DNA synthesis at 15 µmol scale and labeled with Dy396XL at the 5'-end without prior purification. The first two panels show UPLC chromatograms of the DNA before and after reaction for 15 min. Comparison of the starting material and product peak areas indicated ~95% conversion to product. The third panel shows the overlayed absorption spectra of starting material and product.
Figure 9B:
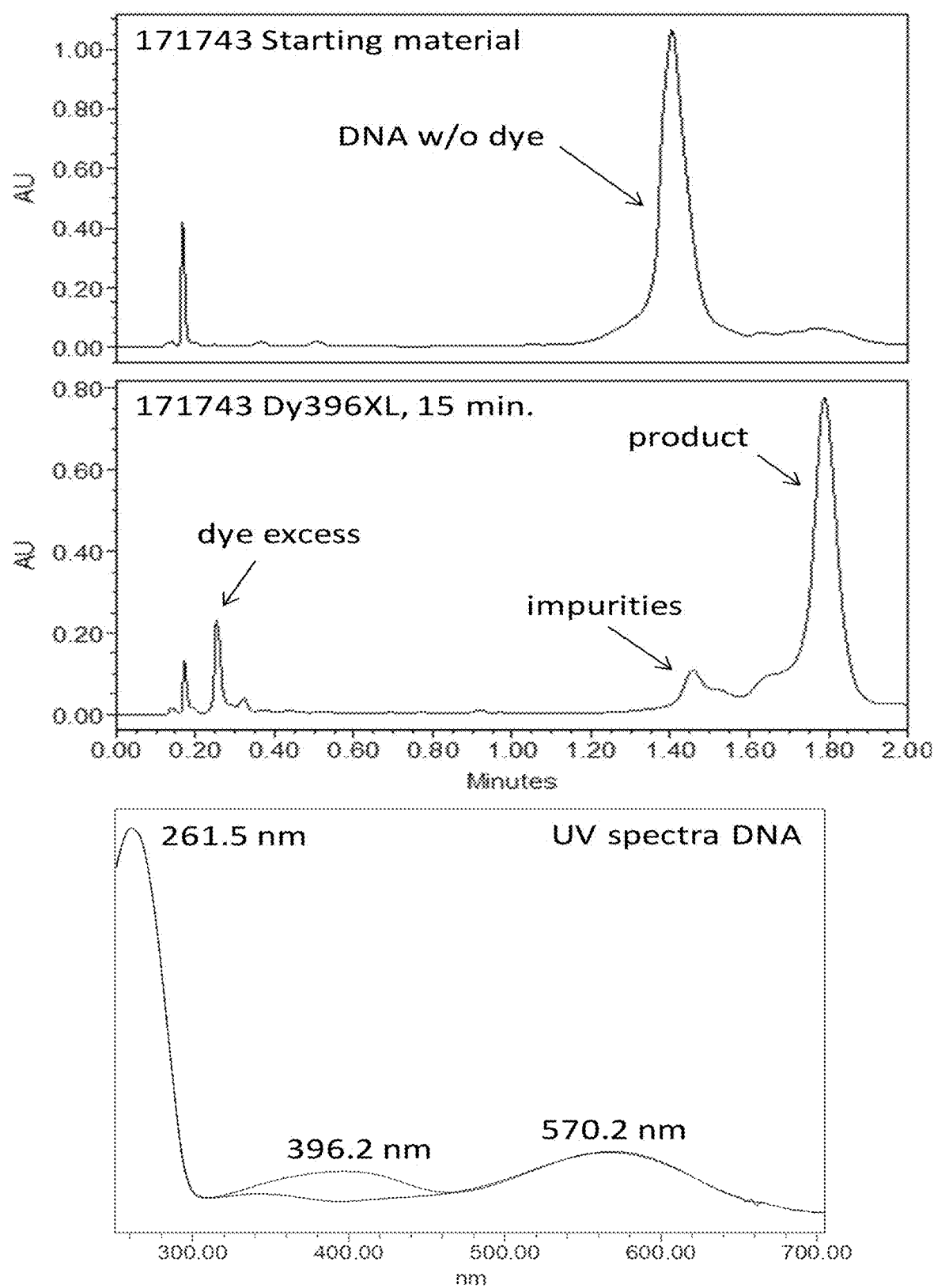
FIG. 9B shows the reproducibility of the large-scale DNA labeling reaction. Shown are UPLC chromatograms for a reaction with the same DNA sequence and under identical conditions as in FIG. 9A, however with a different synthesis batch of fluorescent dye.
Figure 10A:
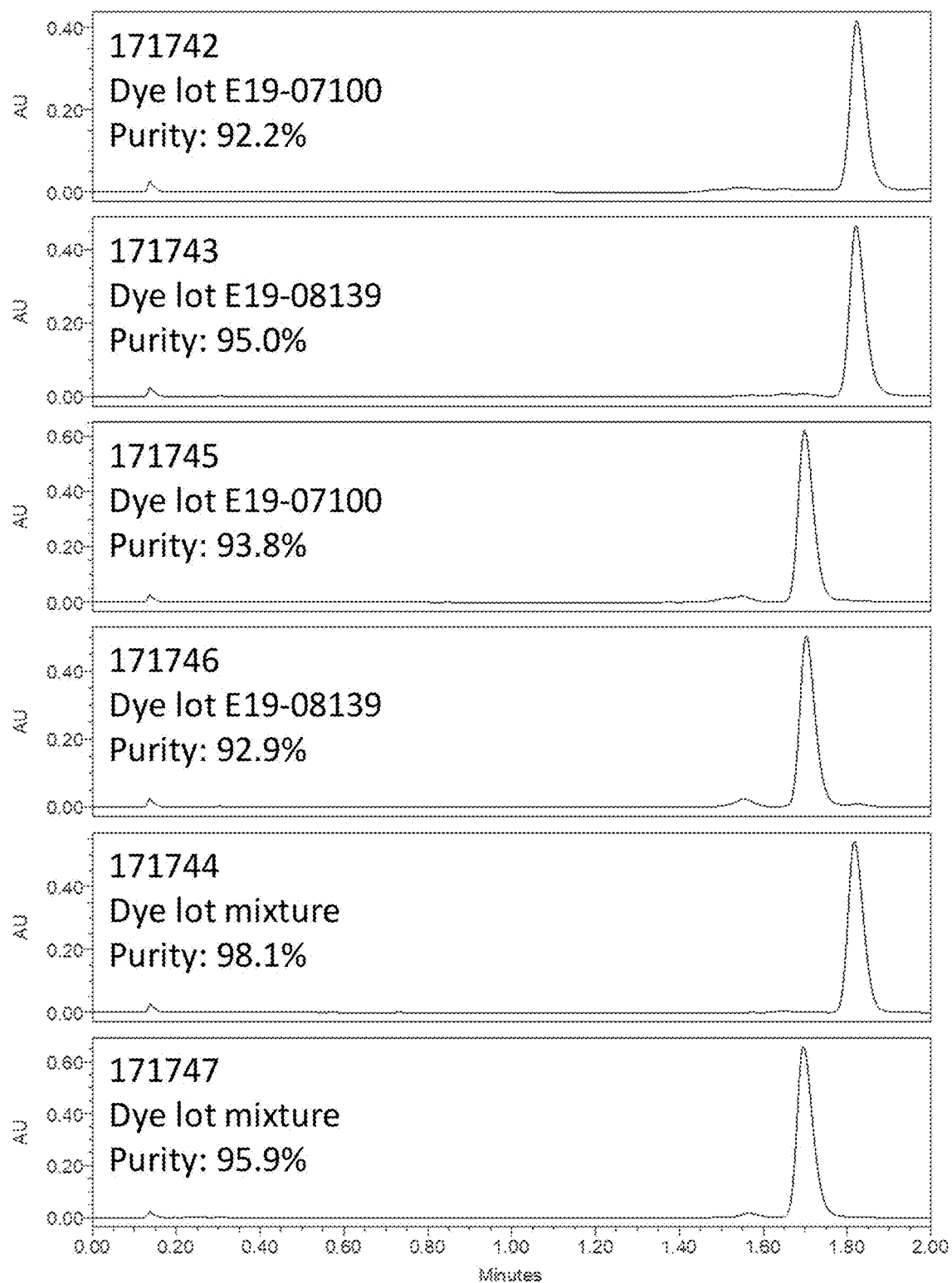
FIG. 10A shows UPLC chromatograms of purified DNA oligonucleotide probes obtained by six independent large-scale labeling reactions using DMT-MM as described in Example 3. Oligonucleotide sequence lengths were 30mer (171742, 171743, 171744) and 33mer (171744, 171745, 171747), each containing a 3'-BHQ-2 quencher.

Results: The labeling efficiencies for two representative large-scale labeling reactions, each using a different synthesis batch of fluorescent dye (Dy396XL), were measured with UPLC and are shown in FIG. 9A and FIG. 9B. The purities and integrities of the purified products were determined with UPLC-MS. The final purity analysis of DNA probes obtained from six large-scale labeling reactions and their measured molecular weights are shown in FIG. 10A and FIG. 10B. The functual analyses of the labeled DNA probes were performed as described Example 2 and are shown in FIG. 11.

What is claimed is:

1. A method for post-synthetic modification of a nucleic acid with a detectable label comprising the steps of:
   (a) preparing an amino-modified nucleic acid molecule comprising one or more amino-modifications;
   (b) activating a carboxy-modified label with a 4-(4,6-dimethoxy-1,3,5-triazin-2-yl)-4-methylmorpholinium (DMT-MM) cation in the presence of a counter anion which is a weakly-coordinating or non-coordinating anion selected from tetrafluoroborate ($BF4^-$) or hexafluorophosphate ($PF6^-$); and
   (c) reacting the amino-modified nucleic acid molecule with the activated carboxy-modified label to generate a labeled nucleic acid molecule.

2. The method of claim 1 wherein the nucleic acid molecule is an oligonucleotide.

3. The method of claim 2 wherein the oligonucleotide is amino-modified at the 5' terminus or at the 3' terminus.

4. The method of claim 2 wherein the oligonucleotide is amino-modified internally.

5. The method of claim 2 wherein the oligonucleotide is synthesized using phosphoramidite-based DNA synthesis.

6. The method of claim 5 wherein the oligonucleotide is purified after synthesis.

7. The method of claim 5 wherein the oligonucleotide is not purified after synthesis.

8. The method of claim 1 wherein the detectable label is selected from the group consisting of a fluorescent dye, a luminescent dye, a quenching dye, a phosphorescent dye, and an affinity tag.

9. The method of claim 8 wherein the detectable label is a fluorescent dye.

10. The method of claim 9 wherein the fluorescent dye is inherently incompatible with phosphoramidite-based DNA synthesis.

11. The method of claim 10 wherein the fluorescent dye contains a sulfonate moiety.

12. The method of claim 1 wherein the steps are conducted during oligonucleotide synthesis and wherein the oligonucleotide is bound on a solid support.

13. The method of claim 1 wherein the nucleic acid molecule is an enzymatically amplified product.

14. The method of claim 1 wherein the nucleic acid molecule is single-stranded.

15. The method of claim 1 wherein the nucleic acid is double stranded.

16. The method of claim 1 wherein the nucleic acid molecule is selected from the group consisting of DNA, RNA, Locked Nucleic Acid (LNA), Peptide Nucleic Acid (PNA), a nucleic acid analog, and hybrid mixtures of DNA, RNA, LNA, PNA, and nucleic acid analogs.

17. A kit comprising a labeled nucleic acid that is labeled by performing the method of claim 1.

* * * * *